United States Patent
Berkman et al.

(10) Patent No.: US 8,912,908 B2
(45) Date of Patent: Dec. 16, 2014

(54) COMMUNICATION SYSTEM WITH REMOTE ACTIVATION

(75) Inventors: Jeffrey Berkman, Saratoga, CA (US); Mark Zdeblick, Portola Valley, CA (US); Patricia Johnson, Palo Alto, CA (US); Hooman Hafezi, Redwood City, CA (US); Jonathan Withrington, San Francisco, CA (US)

(73) Assignee: Proteus Digital Health, Inc., Redwood City, CA (US)

( * ) Notice: Subject to any disclaimer, the term of this patent is extended or adjusted under 35 U.S.C. 154(b) by 286 days.

(21) Appl. No.: 13/180,516

(22) Filed: Jul. 11, 2011

(65) Prior Publication Data

US 2012/0007734 A1    Jan. 12, 2012

(51) Int. Cl.
| | |
|---|---|
| *H04Q 5/22* | (2006.01) |
| *A61J 3/00* | (2006.01) |
| *A61B 5/07* | (2006.01) |
| *H01Q 1/27* | (2006.01) |
| *A61B 5/053* | (2006.01) |
| *A61B 5/03* | (2006.01) |
| *A61B 5/145* | (2006.01) |
| *A61B 5/00* | (2006.01) |

(52) U.S. Cl.
CPC .......... *A61J 3/007* (2013.01); *A61B 2560/0214* (2013.01); *A61B 5/0538* (2013.01); *A61B 5/036* (2013.01); *A61B 5/14539* (2013.01); *A61B 5/0008* (2013.01); *A61B 5/0002* (2013.01); *A61B 5/073* (2013.01); *A61B 5/4839* (2013.01); *H01Q 1/273* (2013.01)
USPC ..................... 340/573.1; 340/10.1; 340/572.8

(58) Field of Classification Search
None
See application file for complete search history.

(56) References Cited

U.S. PATENT DOCUMENTS

| | | |
|---|---|---|
| 3,589,943 A | 6/1971 | Grubb et al. |
| 3,607,788 A | 9/1971 | Adolph |
| 3,642,008 A | 2/1972 | Bolduc |
| 3,679,480 A | 7/1972 | Brown et al. |
| 3,682,160 A | 8/1972 | Murata |
| 3,719,183 A | 3/1973 | Schwartz |
| 3,799,802 A | 3/1974 | Schneble, Jr. et al. |
| 3,828,766 A | 8/1974 | Krasnow |

(Continued)

FOREIGN PATENT DOCUMENTS

| | | |
|---|---|---|
| EP | 0344939 | 12/1989 |
| EP | 1246356 | 10/2002 |

(Continued)

OTHER PUBLICATIONS

Trutag, Technologies, Inc., Spectral Microtags for Authentication and Anti-Counterfeiting; "Product Authentication and Brand Protection Solutions"; http://www.trutags.com/; downloaded Feb. 12, 2013; 1 pp.

(Continued)

*Primary Examiner* — Mohammad Ghayour
*Assistant Examiner* — Brian Wilson
(74) *Attorney, Agent, or Firm* — K&L Gates LLP

(57) ABSTRACT

The system of the present invention includes a conductive element, an electronic component, and a partial power source in the form of dissimilar materials. Upon contact with a conducting fluid, a voltage potential is created and the power source is completed, which activates the system. The electronic component controls the conductance between the dissimilar materials to produce a unique current signature. The system can also measure the conditions of the environment surrounding the system.

9 Claims, 4 Drawing Sheets

(56) References Cited

U.S. PATENT DOCUMENTS

| | | | |
|---|---|---|---|
| 3,837,339 A | 9/1974 | Aisenberg et al. | |
| 3,893,111 A | 7/1975 | Cotter | |
| 3,944,064 A | 3/1976 | Bashaw et al. | |
| 3,967,202 A | 6/1976 | Batz | |
| 3,989,050 A | 11/1976 | Buchalter | |
| 4,017,856 A | 4/1977 | Wiegand | |
| 4,055,178 A | 10/1977 | Harrigan | |
| 4,062,750 A | 12/1977 | Butler | |
| 4,077,397 A | 3/1978 | Ellis | |
| 4,077,398 A | 3/1978 | Ellis | |
| 4,082,087 A | 4/1978 | Howson | |
| 4,090,752 A | 5/1978 | Long | |
| 4,106,348 A | 8/1978 | Auphan | |
| 4,129,125 A | 12/1978 | Lester | |
| 4,166,453 A | 9/1979 | McClelland | |
| 4,239,046 A | 12/1980 | Ong | |
| 4,251,795 A | 2/1981 | Shibasaki et al. | |
| 4,269,189 A | 5/1981 | Abraham | |
| 4,331,654 A | 5/1982 | Morris | |
| 4,345,588 A | 8/1982 | Widder et al. | |
| 4,418,697 A | 12/1983 | Tama | |
| 4,425,117 A | 1/1984 | Hugemann | |
| 4,439,196 A | 3/1984 | Higuchi | |
| 4,494,950 A | 1/1985 | Fischell | |
| 4,559,950 A | 12/1985 | Vaughan | |
| 4,564,363 A | 1/1986 | Bagnall et al. | |
| 4,578,061 A | 3/1986 | Lemelson | |
| 4,635,641 A | 1/1987 | Hoffman | |
| 4,654,165 A | 3/1987 | Eisenberg | |
| 4,663,250 A | 5/1987 | Ong et al. | |
| 4,669,479 A | 6/1987 | Dunseath | |
| 4,681,111 A | 7/1987 | Silvian | |
| 4,687,660 A | 8/1987 | Baker et al. | |
| 4,725,997 A | 2/1988 | Urquhart et al. | |
| 4,763,659 A | 8/1988 | Dunseath | |
| 4,767,627 A | 8/1988 | Caldwell et al. | |
| 4,784,162 A | 11/1988 | Ricks | |
| 4,793,825 A | 12/1988 | Benjamin et al. | |
| 4,844,076 A | 7/1989 | Lesho | |
| 4,876,093 A | 10/1989 | Theeuwes et al. | |
| 4,896,261 A | 1/1990 | Nolan | |
| 4,975,230 A | 12/1990 | Pinkhasov | |
| 4,987,897 A | 1/1991 | Funke | |
| 5,000,957 A | 3/1991 | Eckenhoff et al. | |
| 5,016,634 A | 5/1991 | Vock et al. | |
| 5,079,006 A | 1/1992 | Urquhart | |
| 5,167,626 A | 12/1992 | Casper | |
| 5,176,626 A | 1/1993 | Soehendra | |
| 5,261,402 A | 11/1993 | DiSabito | |
| 5,263,481 A | 11/1993 | Axelgaard et al. | |
| 5,281,287 A | 1/1994 | Lloyd | |
| 5,283,136 A | 2/1994 | Peled et al. | |
| 5,305,745 A | 4/1994 | Zacouto | |
| 5,318,557 A | 6/1994 | Gross | |
| 5,394,882 A | 3/1995 | Mawhinney | |
| 5,395,366 A | 3/1995 | D'Andrea et al. | |
| 5,436,091 A | 7/1995 | Shackle et al. | |
| 5,443,461 A | 8/1995 | Atkinson et al. | |
| 5,443,843 A | 8/1995 | Curatolo et al. | |
| 5,458,141 A | 10/1995 | Neil et al. | |
| 5,485,841 A | 1/1996 | Watkin et al. | |
| 5,567,210 A | 10/1996 | Bates et al. | |
| 5,596,302 A | 1/1997 | Mastrocola et al. | |
| 5,600,548 A | 2/1997 | Nguyen et al. | |
| 5,634,466 A | 6/1997 | Gruner | |
| 5,634,468 A | 6/1997 | Platt | |
| 5,645,063 A | 7/1997 | Straka et al. | |
| 5,705,189 A | 1/1998 | Lehmann et al. | |
| 5,738,708 A | 4/1998 | Peachey et al. | |
| 5,740,811 A | 4/1998 | Hedberg | |
| 5,757,326 A | 5/1998 | Koyama et al. | |
| 5,792,048 A | 8/1998 | Schaefer | |
| 5,802,467 A | 9/1998 | Salazar | |
| 5,833,716 A | 11/1998 | Bar-Or | |
| 5,845,265 A | 12/1998 | Woolston | |
| 5,862,803 A | 1/1999 | Besson | |
| 5,862,808 A | 1/1999 | Albarello | |
| 5,868,136 A | 2/1999 | Fox | |
| 5,925,030 A | 7/1999 | Gross et al. | |
| 5,925,066 A | 7/1999 | Kroll et al. | |
| 5,957,854 A | 9/1999 | Besson et al. | |
| 5,963,132 A | 10/1999 | Yoakum | |
| 5,974,124 A | 10/1999 | Schlueter, Jr. et al. | |
| 5,981,166 A | 11/1999 | Mandecki | |
| 5,999,846 A | 12/1999 | Pardey et al. | |
| 6,038,464 A | 3/2000 | Axelgaard et al. | |
| 6,042,710 A | 3/2000 | Dubrow | |
| 6,047,203 A | 4/2000 | Sackner | |
| 6,076,016 A * | 6/2000 | Feierbach | 607/32 |
| 6,081,734 A | 6/2000 | Batz | |
| 6,083,248 A | 7/2000 | Thompson | |
| 6,091,975 A | 7/2000 | Daddona et al. | |
| 6,095,985 A | 8/2000 | Raymond et al. | |
| 6,115,636 A | 9/2000 | Ryan | |
| 6,122,351 A | 9/2000 | Schlueter, Jr. et al. | |
| 6,141,592 A | 10/2000 | Pauly | |
| 6,149,940 A | 11/2000 | Maggi et al. | |
| 6,200,265 B1 | 3/2001 | Walsh et al. | |
| 6,206,702 B1 | 3/2001 | Hayden et al. | |
| 6,217,744 B1 | 4/2001 | Crosby | |
| 6,231,593 B1 | 5/2001 | Meserol | |
| 6,245,057 B1 | 6/2001 | Sieben et al. | |
| 6,269,058 B1 | 7/2001 | Yamanoi et al. | |
| 6,285,897 B1 | 9/2001 | Kilcoyne et al. | |
| 6,287,252 B1 | 9/2001 | Lugo | |
| 6,288,629 B1 | 9/2001 | Cofino et al. | |
| 6,289,238 B1 | 9/2001 | Besson et al. | |
| 6,315,719 B1 | 11/2001 | Rode et al. | |
| 6,342,774 B1 | 1/2002 | Kreisinger et al. | |
| 6,358,202 B1 | 3/2002 | Arent | |
| 6,364,834 B1 | 4/2002 | Reuss | |
| 6,366,206 B1 | 4/2002 | Ishikawa et al. | |
| 6,368,190 B1 | 4/2002 | Easter et al. | |
| 6,371,927 B1 | 4/2002 | Brune | |
| 6,374,670 B1 | 4/2002 | Spelman | |
| 6,380,858 B1 | 4/2002 | Yarin et al. | |
| 6,390,088 B1 | 5/2002 | Noehl et al. | |
| 6,394,997 B1 | 5/2002 | Lemelson | |
| 6,426,863 B1 | 7/2002 | Munshi | |
| 6,432,292 B1 | 8/2002 | Pinto et al. | |
| 6,440,069 B1 | 8/2002 | Raymond et al. | |
| 6,441,747 B1 | 8/2002 | Khair | |
| 6,453,199 B1 | 9/2002 | Kobozev | |
| 6,477,424 B1 | 11/2002 | Thompson et al. | |
| 6,494,829 B1 | 12/2002 | New et al. | |
| 6,496,705 B1 | 12/2002 | Ng et al. | |
| 6,526,315 B1 | 2/2003 | Inagawa | |
| 6,531,026 B1 | 3/2003 | Takeichi et al. | |
| 6,544,174 B2 | 4/2003 | West | |
| 6,564,079 B1 | 5/2003 | Cory | |
| 6,572,636 B1 | 6/2003 | Hagen et al. | |
| 6,577,893 B1 | 6/2003 | Besson et al. | |
| 6,579,231 B1 | 6/2003 | Phipps | |
| 6,595,929 B2 | 7/2003 | Stivoric | |
| 6,599,284 B2 | 7/2003 | Faour et al. | |
| 6,605,038 B1 | 8/2003 | Teller | |
| 6,609,018 B2 | 8/2003 | Cory | |
| 6,612,984 B1 | 9/2003 | Kerr | |
| 6,632,175 B1 | 10/2003 | Marshall | |
| 6,632,216 B2 | 10/2003 | Houzego et al. | |
| 6,635,279 B2 | 10/2003 | Kolter et al. | |
| 6,643,541 B2 | 11/2003 | Mok et al. | |
| 6,654,638 B1 | 11/2003 | Sweeney | |
| 6,663,846 B1 | 12/2003 | McCombs | |
| 6,673,474 B2 | 1/2004 | Yamamoto | |
| 6,680,923 B1 | 1/2004 | Leon | |
| 6,689,117 B2 | 2/2004 | Sweeney et al. | |
| 6,694,161 B2 | 2/2004 | Mehrotra | |
| 6,704,602 B2 | 3/2004 | Berg et al. | |
| 6,720,923 B1 | 4/2004 | Hayward et al. | |
| 6,738,671 B2 | 5/2004 | Christophersom et al. | |
| 6,740,033 B1 | 5/2004 | Olejniczak et al. | |
| 6,745,082 B2 | 6/2004 | Axelgaard et al. | |
| 6,755,783 B2 | 6/2004 | Cosentino | |

(56) References Cited

U.S. PATENT DOCUMENTS

| | | |
|---|---|---|
| 6,757,523 B2 | 6/2004 | Fry |
| 6,759,968 B2 | 7/2004 | Zierolf |
| 6,773,429 B2 | 8/2004 | Sheppard et al. |
| 6,800,060 B2 | 10/2004 | Marshall |
| 6,801,137 B2 | 10/2004 | Eggers et al. |
| 6,814,706 B2 | 11/2004 | Barton et al. |
| 6,822,554 B2 | 11/2004 | Vrijens et al. |
| 6,836,862 B1 | 12/2004 | Erekson et al. |
| 6,839,659 B2 | 1/2005 | Tarassenko et al. |
| 6,840,904 B2 | 1/2005 | Goldberg |
| 6,842,636 B2 | 1/2005 | Perrault |
| 6,845,272 B1 | 1/2005 | Thomsen |
| 6,864,780 B2 | 3/2005 | Doi |
| 6,879,810 B2 | 4/2005 | Bouet |
| 6,882,881 B1 | 4/2005 | Lesser et al. |
| 6,897,788 B2 | 5/2005 | Khair et al. |
| 6,909,878 B2 | 6/2005 | Haller |
| 6,922,592 B2 | 7/2005 | Thompson et al. |
| 6,928,370 B2 | 8/2005 | Anuzis et al. |
| 6,929,636 B1 | 8/2005 | Von Alten |
| 6,937,150 B2 | 8/2005 | Medema |
| 6,942,616 B2 | 9/2005 | Kerr |
| 6,951,536 B2 | 10/2005 | Yokoi |
| 6,957,107 B2 | 10/2005 | Rogers et al. |
| 6,959,929 B2 | 11/2005 | Pugnet et al. |
| 6,968,153 B1 | 11/2005 | Heinonen |
| 6,987,965 B2 | 1/2006 | Ng et al. |
| 6,990,082 B1 | 1/2006 | Zehavi et al. |
| 7,002,476 B2 | 2/2006 | Rapchak |
| 7,004,395 B2 | 2/2006 | Koenck |
| 7,009,634 B2 | 3/2006 | Iddan et al. |
| 7,009,946 B1 | 3/2006 | Kardach |
| 7,013,162 B2 | 3/2006 | Gorsuch |
| 7,016,648 B2 | 3/2006 | Haller |
| 7,020,508 B2 | 3/2006 | Stivoric |
| 7,024,248 B2 | 4/2006 | Penner et al. |
| 7,031,745 B2 | 4/2006 | Shen |
| 7,031,857 B2 | 4/2006 | Tarassenko et al. |
| 7,039,453 B2 | 5/2006 | Mullick |
| 7,044,911 B2 | 5/2006 | Drinan et al. |
| 7,046,649 B2 | 5/2006 | Awater et al. |
| 7,118,531 B2 | 10/2006 | Krill |
| 7,127,300 B2 | 10/2006 | Mazar et al. |
| 7,146,228 B2 | 12/2006 | Nielsen |
| 7,146,449 B2 | 12/2006 | Do et al. |
| 7,149,581 B2 | 12/2006 | Goedeke et al. |
| 7,154,071 B2 | 12/2006 | Sattler et al. |
| 7,155,232 B2 | 12/2006 | Godfrey et al. |
| 7,160,258 B2 | 1/2007 | Imran |
| 7,161,484 B2 | 1/2007 | Tsoukalis |
| 7,164,942 B2 | 1/2007 | Avrahami |
| 7,171,166 B2 | 1/2007 | Ng et al. |
| 7,171,177 B2 | 1/2007 | Park et al. |
| 7,171,259 B2 | 1/2007 | Rytky |
| 7,176,784 B2 | 2/2007 | Gilbert et al. |
| 7,187,960 B2 | 3/2007 | Abreu |
| 7,188,767 B2 | 3/2007 | Penuela |
| 7,194,038 B1 | 3/2007 | Inkinen |
| 7,206,630 B1 | 4/2007 | Tarler |
| 7,209,790 B2 | 4/2007 | Thompson et al. |
| 7,215,660 B2 | 5/2007 | Perlman |
| 7,215,991 B2 | 5/2007 | Besson |
| 7,218,967 B2 | 5/2007 | Bergelson |
| 7,231,451 B2 | 6/2007 | Law |
| 7,243,118 B2 | 7/2007 | Lou |
| 7,246,521 B2 | 7/2007 | Kim |
| 7,249,212 B2 | 7/2007 | Do |
| 7,252,792 B2 | 8/2007 | Perrault |
| 7,253,716 B2 | 8/2007 | Lovoi et al. |
| 7,261,690 B2 | 8/2007 | Teller |
| 7,270,633 B1 | 9/2007 | Goscha |
| 7,273,454 B2 | 9/2007 | Raymond et al. |
| 7,285,090 B2 | 10/2007 | Stivoric et al. |
| 7,289,855 B2 | 10/2007 | Nghiem |
| 7,291,497 B2 | 11/2007 | Holmes |
| 7,292,139 B2 | 11/2007 | Mazar et al. |
| 7,294,105 B1 | 11/2007 | Islam |
| 7,313,163 B2 | 12/2007 | Liu |
| 7,317,378 B2 | 1/2008 | Jarvis et al. |
| 7,318,808 B2 | 1/2008 | Tarassenko et al. |
| 7,336,929 B2 | 2/2008 | Yasuda |
| 7,342,895 B2 | 3/2008 | Serpa |
| 7,346,380 B2 | 3/2008 | Axelgaard et al. |
| 7,349,722 B2 | 3/2008 | Witkowski et al. |
| 7,352,998 B2 | 4/2008 | Palin |
| 7,353,258 B2 | 4/2008 | Washburn |
| 7,357,891 B2 | 4/2008 | Yang et al. |
| 7,359,674 B2 | 4/2008 | Markki |
| 7,366,558 B2 | 4/2008 | Virtanen et al. |
| 7,368,190 B2 | 5/2008 | Heller et al. |
| 7,368,191 B2 | 5/2008 | Andelman et al. |
| 7,373,196 B2 | 5/2008 | Ryu et al. |
| 7,375,739 B2 | 5/2008 | Robbins |
| 7,376,435 B2 | 5/2008 | McGowan |
| 7,382,263 B2 | 6/2008 | Danowski et al. |
| 7,387,607 B2 | 6/2008 | Holt |
| 7,388,903 B2 | 6/2008 | Godfrey et al. |
| 7,389,088 B2 | 6/2008 | Kim |
| 7,392,015 B1 | 6/2008 | Farlow |
| 7,395,106 B2 | 7/2008 | Ryu et al. |
| 7,396,330 B2 | 7/2008 | Banet |
| 7,404,968 B2 | 7/2008 | Abrams et al. |
| 7,413,544 B2 | 8/2008 | Kerr |
| 7,414,534 B1 | 8/2008 | Kroll et al. |
| 7,414,543 B2 | 8/2008 | Rye et al. |
| 7,415,242 B1 | 8/2008 | Ngan |
| 7,424,268 B2 | 9/2008 | Diener |
| 7,424,319 B2 | 9/2008 | Muehlsteff |
| 7,427,266 B2 | 9/2008 | Ayer et al. |
| 7,471,665 B2 | 12/2008 | Perlman |
| 7,499,674 B2 | 3/2009 | Salokannel |
| 7,502,643 B2 | 3/2009 | Farringdon et al. |
| 7,505,795 B1 | 3/2009 | Lim et al. |
| 7,510,121 B2 | 3/2009 | Koenck |
| 7,512,448 B2 | 3/2009 | Malick |
| 7,515,043 B2 | 4/2009 | Welch |
| 7,519,416 B2 | 4/2009 | Sula et al. |
| 7,523,756 B2 | 4/2009 | Minai |
| 7,525,426 B2 | 4/2009 | Edelstein |
| 7,539,533 B2 | 5/2009 | Tran |
| 7,542,878 B2 | 6/2009 | Nanikashvili |
| 7,551,590 B2 | 6/2009 | Haller |
| 7,554,452 B2 | 6/2009 | Cole |
| 7,558,620 B2 | 7/2009 | Ishibashi |
| 7,575,005 B2 | 8/2009 | Mumford |
| 7,616,111 B2 | 11/2009 | Covannon |
| 7,617,001 B2 | 11/2009 | Penner et al. |
| 7,639,473 B2 | 12/2009 | Hsu et al. |
| 7,640,802 B2 | 1/2010 | King et al. |
| 7,647,112 B2 | 1/2010 | Tracey |
| 7,647,185 B2 | 1/2010 | Tarassenko et al. |
| 7,653,031 B2 | 1/2010 | Godfrey et al. |
| 7,668,437 B1 | 2/2010 | Yamada et al. |
| 7,672,703 B2 | 3/2010 | Yeo et al. |
| 7,672,714 B2 | 3/2010 | Kuo |
| 7,673,679 B2 | 3/2010 | Harrison et al. |
| 7,678,043 B2 | 3/2010 | Gilad |
| 7,689,437 B1 | 3/2010 | Teller et al. |
| 7,697,994 B2 | 4/2010 | VanDanacker et al. |
| 7,720,036 B2 | 5/2010 | Sadri |
| 7,729,776 B2 | 6/2010 | Von Arx et al. |
| 7,733,224 B2 | 6/2010 | Tran |
| 7,736,318 B2 | 6/2010 | Cosentino |
| 7,756,587 B2 | 7/2010 | Penner et al. |
| 7,796,043 B2 | 9/2010 | Euliano et al. |
| 7,797,033 B2 | 9/2010 | D'Andrea et al. |
| 7,809,399 B2 | 10/2010 | Lu |
| 7,844,341 B2 | 11/2010 | Von Arx et al. |
| 8,073,707 B2 | 12/2011 | Teller et al. |
| 8,258,962 B2 | 9/2012 | Robertson et al. |
| 8,389,003 B2 | 3/2013 | Mintchev et al. |
| 8,597,186 B2 | 12/2013 | Hafezi et al. |
| 2001/0027331 A1 | 10/2001 | Thompson |
| 2001/0044588 A1 | 11/2001 | Mault |

(56) References Cited

U.S. PATENT DOCUMENTS

| | | |
|---|---|---|
| 2001/0051766 A1 | 12/2001 | Gazdzinski |
| 2002/0002326 A1 | 1/2002 | Causey et al. |
| 2002/0026111 A1 | 2/2002 | Ackerman |
| 2002/0032384 A1 | 3/2002 | Raymond et al. |
| 2002/0032385 A1 | 3/2002 | Raymond et al. |
| 2002/0040278 A1 | 4/2002 | Anuzis et al. |
| 2002/0077620 A1 | 6/2002 | Sweeney et al. |
| 2002/0132226 A1 | 9/2002 | Nair |
| 2002/0192159 A1 | 12/2002 | Reitberg |
| 2002/0193669 A1 | 12/2002 | Glukhovsky |
| 2002/0198470 A1 | 12/2002 | Imran et al. |
| 2003/0017826 A1 | 1/2003 | Fishman |
| 2003/0023150 A1 | 1/2003 | Yokoi et al. |
| 2003/0028226 A1 | 2/2003 | Thompson |
| 2003/0065536 A1 | 4/2003 | Hansen |
| 2003/0076179 A1 | 4/2003 | Branch et al. |
| 2003/0083559 A1 | 5/2003 | Thompson |
| 2003/0126593 A1 | 7/2003 | Mault |
| 2003/0130714 A1 | 7/2003 | Nielsen et al. |
| 2003/0135128 A1 | 7/2003 | Suffin et al. |
| 2003/0135392 A1 | 7/2003 | Vrijens et al. |
| 2003/0152622 A1 | 8/2003 | Louie-Helm et al. |
| 2003/0158466 A1 | 8/2003 | Lynn et al. |
| 2003/0158756 A1 | 8/2003 | Abramson |
| 2003/0162556 A1 | 8/2003 | Libes |
| 2003/0167000 A1 | 9/2003 | Mullick et al. |
| 2003/0171791 A1 | 9/2003 | KenKnight |
| 2003/0171898 A1 | 9/2003 | Tarassenko et al. |
| 2003/0181788 A1 | 9/2003 | Yokoi et al. |
| 2003/0185286 A1 | 10/2003 | Yuen |
| 2003/0187337 A1 | 10/2003 | Tarassenko et al. |
| 2003/0187338 A1 | 10/2003 | Say et al. |
| 2003/0195403 A1 | 10/2003 | Berner et al. |
| 2003/0213495 A1 | 11/2003 | Fujita et al. |
| 2003/0214579 A1 | 11/2003 | Iddan |
| 2003/0216622 A1 | 11/2003 | Meron et al. |
| 2003/0216625 A1 | 11/2003 | Phipps |
| 2003/0216666 A1 | 11/2003 | Ericson et al. |
| 2003/0216729 A1 | 11/2003 | Marchitto |
| 2003/0232895 A1 | 12/2003 | Omidian et al. |
| 2004/0008123 A1 | 1/2004 | Carrender et al. |
| 2004/0018476 A1 | 1/2004 | LaDue |
| 2004/0034295 A1 | 2/2004 | Salganicoff |
| 2004/0049245 A1 | 3/2004 | Gass |
| 2004/0073095 A1 | 4/2004 | Causey et al. |
| 2004/0073454 A1 | 4/2004 | Urquhart et al. |
| 2004/0077995 A1 | 4/2004 | Ferek-Petric |
| 2004/0082982 A1 | 4/2004 | Gord et al. |
| 2004/0087839 A1 | 5/2004 | Raymond et al. |
| 2004/0092801 A1 | 5/2004 | Drakulic |
| 2004/0106859 A1 | 6/2004 | Say et al. |
| 2004/0115517 A1 | 6/2004 | Fukuda et al. |
| 2004/0121015 A1 | 6/2004 | Chidlaw et al. |
| 2004/0122297 A1 | 6/2004 | Stahmann et al. |
| 2004/0148140 A1 | 7/2004 | Tarassenko et al. |
| 2004/0153007 A1 | 8/2004 | Harris |
| 2004/0167226 A1 | 8/2004 | Serafini |
| 2004/0167801 A1 | 8/2004 | Say et al. |
| 2004/0193020 A1 | 9/2004 | Chiba |
| 2004/0193029 A1 | 9/2004 | Glukhovsky |
| 2004/0193446 A1 | 9/2004 | Mayer et al. |
| 2004/0199222 A1 | 10/2004 | Sun et al. |
| 2004/1215084 | 10/2004 | Shimizu et al. |
| 2004/0218683 A1 | 11/2004 | Batra |
| 2004/0220643 A1 | 11/2004 | Schmidt |
| 2004/0224644 A1 | 11/2004 | Wu |
| 2004/0225199 A1 | 11/2004 | Evanyk |
| 2004/0253304 A1* | 12/2004 | Gross et al. ............ 424/451 |
| 2004/0258571 A1 | 12/2004 | Lee et al. |
| 2004/0260154 A1 | 12/2004 | Sidelnik |
| 2005/0017841 A1 | 1/2005 | Doi |
| 2005/0020887 A1 | 1/2005 | Goldberg |
| 2005/0021103 A1 | 1/2005 | DiLorenzo |
| 2005/0021370 A1 | 1/2005 | Riff |
| 2005/0024198 A1 | 2/2005 | Ward |
| 2005/0027205 A1 | 2/2005 | Tarassenko et al. |
| 2005/0038321 A1 | 2/2005 | Fujita et al. |
| 2005/0043634 A1 | 2/2005 | Yokoi et al. |
| 2005/0043894 A1 | 2/2005 | Fernandez |
| 2005/0054897 A1 | 3/2005 | Hashimoto et al. |
| 2005/0055014 A1 | 3/2005 | Coppeta et al. |
| 2005/0062644 A1 | 3/2005 | Leci |
| 2005/0065407 A1 | 3/2005 | Nakamura et al. |
| 2005/0070778 A1 | 3/2005 | Lackey |
| 2005/0090753 A1 | 4/2005 | Goor et al. |
| 2005/0092108 A1 | 5/2005 | Andermo |
| 2005/0096514 A1 | 5/2005 | Starkebaum |
| 2005/0096562 A1 | 5/2005 | Delalic et al. |
| 2005/0101843 A1 | 5/2005 | Quinn |
| 2005/0101872 A1 | 5/2005 | Sattler |
| 2005/0115561 A1 | 6/2005 | Stahmann et al. |
| 2005/0116820 A1 | 6/2005 | Goldreich |
| 2005/0117389 A1 | 6/2005 | Worledge |
| 2005/0121322 A1 | 6/2005 | Say et al. |
| 2005/0131281 A1 | 6/2005 | Ayer et al. |
| 2005/0143623 A1 | 6/2005 | Kojima |
| 2005/0148883 A1 | 7/2005 | Boesen |
| 2005/0154428 A1 | 7/2005 | Bruinsma |
| 2005/0156709 A1 | 7/2005 | Gilbert et al. |
| 2005/0165323 A1 | 7/2005 | Montgomery |
| 2005/0177069 A1 | 8/2005 | Takizawa |
| 2005/0182389 A1 | 8/2005 | LaPorte |
| 2005/0187789 A1 | 8/2005 | Hatlestad et al. |
| 2005/0192489 A1 | 9/2005 | Marshall |
| 2005/0197680 A1 | 9/2005 | DelMain et al. |
| 2005/0228268 A1 | 10/2005 | Cole |
| 2005/0234307 A1 | 10/2005 | Heinonen |
| 2005/0240305 A1 | 10/2005 | Bogash et al. |
| 2005/0245794 A1 | 11/2005 | Dinsmoor |
| 2005/0245839 A1 | 11/2005 | Stivoric et al. |
| 2005/0259768 A1 | 11/2005 | Yang et al. |
| 2005/0261559 A1 | 11/2005 | Mumford |
| 2005/0267556 A1 | 12/2005 | Shuros et al. |
| 2005/0267756 A1 | 12/2005 | Schultz et al. |
| 2005/0277912 A1 | 12/2005 | John |
| 2005/0277999 A1 | 12/2005 | Strother et al. |
| 2005/0285746 A1 | 12/2005 | Sengupta |
| 2005/0288594 A1 | 12/2005 | Lewkowicz et al. |
| 2006/0001496 A1 | 1/2006 | Abrosimov et al. |
| 2006/0028727 A1 | 2/2006 | Moon et al. |
| 2006/0036134 A1 | 2/2006 | Tarassenko et al. |
| 2006/0058602 A1 | 3/2006 | Kwiatkowski et al. |
| 2006/0061472 A1 | 3/2006 | Lovoi et al. |
| 2006/0065713 A1 | 3/2006 | Kingery |
| 2006/0068006 A1 | 3/2006 | Begleiter |
| 2006/0074283 A1 | 4/2006 | Henderson |
| 2006/0074319 A1 | 4/2006 | Barnes et al. |
| 2006/0078765 A1 | 4/2006 | Yang et al. |
| 2006/0095091 A1 | 5/2006 | Drew |
| 2006/0095093 A1 | 5/2006 | Bettesh et al. |
| 2006/0100533 A1 | 5/2006 | Han |
| 2006/0109058 A1 | 5/2006 | Keating |
| 2006/0110962 A1 | 5/2006 | Powell |
| 2006/0122474 A1 | 6/2006 | Teller et al. |
| 2006/0122667 A1 | 6/2006 | Chavan et al. |
| 2006/0136266 A1 | 6/2006 | Tarassenko et al. |
| 2006/0142648 A1 | 6/2006 | Banet |
| 2006/0145876 A1 | 7/2006 | Kimura |
| 2006/0148254 A1 | 7/2006 | McLean |
| 2006/0149339 A1 | 7/2006 | Burnes |
| 2006/0155174 A1 | 7/2006 | Glukhovsky et al. |
| 2006/0155183 A1 | 7/2006 | Kroecker |
| 2006/0161225 A1 | 7/2006 | Sormann et al. |
| 2006/0179949 A1 | 8/2006 | Kim |
| 2006/0183993 A1 | 8/2006 | Horn |
| 2006/0184092 A1 | 8/2006 | Atanasoska et al. |
| 2006/0204738 A1 | 9/2006 | Dubrow et al. |
| 2006/0210626 A1 | 9/2006 | Spaeder |
| 2006/0216603 A1 | 9/2006 | Choi |
| 2006/0218011 A1 | 9/2006 | Walker |
| 2006/0235489 A1 | 10/2006 | Drew |
| 2006/0243288 A1 | 11/2006 | Kim et al. |
| 2006/0247505 A1 | 11/2006 | Siddiqui |
| 2006/0253005 A1 | 11/2006 | Drinan |

(56) References Cited

U.S. PATENT DOCUMENTS

| | | |
|---|---|---|
| 2006/0270346 A1 | 11/2006 | Ibrahim |
| 2006/0273882 A1 | 12/2006 | Posamentier |
| 2006/0276702 A1 | 12/2006 | McGinnis |
| 2006/0280227 A1 | 12/2006 | Pinkney |
| 2006/0282001 A1 | 12/2006 | Noel |
| 2006/0289640 A1 | 12/2006 | Mercure |
| 2006/0293607 A1 | 12/2006 | Alt |
| 2007/0000776 A1 | 1/2007 | Karube et al. |
| 2007/0002038 A1 | 1/2007 | Suzuki |
| 2007/0006636 A1 | 1/2007 | King et al. |
| 2007/0008113 A1 | 1/2007 | Spoonhower et al. |
| 2007/0016089 A1 | 1/2007 | Fischell et al. |
| 2007/0027386 A1 | 2/2007 | Such |
| 2007/0027388 A1 | 2/2007 | Chou |
| 2007/0038054 A1 | 2/2007 | Zhou |
| 2007/0049339 A1 | 3/2007 | Barak et al. |
| 2007/0055098 A1 | 3/2007 | Shimizu et al. |
| 2007/0060797 A1 | 3/2007 | Ball |
| 2007/0060800 A1 | 3/2007 | Drinan et al. |
| 2007/0066929 A1 | 3/2007 | Ferren et al. |
| 2007/0073353 A1 | 3/2007 | Rooney et al. |
| 2007/0096765 A1 | 5/2007 | Kagan |
| 2007/0106346 A1 | 5/2007 | Bergelson |
| 2007/0123772 A1 | 5/2007 | Euliano |
| 2007/0129622 A1 | 6/2007 | Bourget |
| 2007/0130287 A1 | 6/2007 | Kumar |
| 2007/0135803 A1 | 6/2007 | Belson |
| 2007/0142721 A1 | 6/2007 | Berner et al. |
| 2007/0156016 A1 | 7/2007 | Betesh |
| 2007/0160789 A1 | 7/2007 | Merical et al. |
| 2007/0162089 A1 | 7/2007 | Mosesov |
| 2007/0162090 A1 | 7/2007 | Penner |
| 2007/0167495 A1 | 7/2007 | Brown et al. |
| 2007/0167848 A1 | 7/2007 | Kuo et al. |
| 2007/0173701 A1 | 7/2007 | Al-Ali |
| 2007/0179347 A1 | 8/2007 | Tarassenko et al. |
| 2007/0179371 A1 | 8/2007 | Peyser et al. |
| 2007/0185393 A1 | 8/2007 | Zhou |
| 2007/0191002 A1 | 8/2007 | Ge |
| 2007/0196456 A1 | 8/2007 | Stevens |
| 2007/0207793 A1 | 9/2007 | Myer |
| 2007/0208233 A1 | 9/2007 | Kovacs |
| 2007/0213659 A1 | 9/2007 | Trovato et al. |
| 2007/0237719 A1 | 10/2007 | Jones |
| 2007/0244370 A1 | 10/2007 | Kuo et al. |
| 2007/0255198 A1 | 11/2007 | Leong et al. |
| 2007/0255330 A1 | 11/2007 | Lee |
| 2007/0270672 A1 | 11/2007 | Hayter |
| 2007/0279217 A1 | 12/2007 | Venkatraman |
| 2007/0282174 A1 | 12/2007 | Sabatino |
| 2007/0282177 A1 | 12/2007 | Pilz |
| 2007/0299480 A1 | 12/2007 | Hill |
| 2008/0014866 A1 | 1/2008 | Lipowshi |
| 2008/0020037 A1 | 1/2008 | Robertson et al. |
| 2008/0021519 A1 | 1/2008 | DeGeest |
| 2008/0021521 A1 | 1/2008 | Shah |
| 2008/0027679 A1 | 1/2008 | Shklarski |
| 2008/0033273 A1 | 2/2008 | Zhou |
| 2008/0038588 A1 | 2/2008 | Lee |
| 2008/0039700 A1 | 2/2008 | Drinan et al. |
| 2008/0045843 A1 | 2/2008 | Tsuji et al. |
| 2008/0046038 A1 | 2/2008 | Hill |
| 2008/0051647 A1 | 2/2008 | Wu et al. |
| 2008/0051667 A1 | 2/2008 | Goldreich |
| 2008/0058614 A1 | 3/2008 | Banet |
| 2008/0062856 A1 | 3/2008 | Feher |
| 2008/0065168 A1 | 3/2008 | Bitton et al. |
| 2008/0074307 A1 | 3/2008 | Boric-Lubecke |
| 2008/0077015 A1 | 3/2008 | Boric-Lubecke |
| 2008/0077028 A1 | 3/2008 | Schaldach et al. |
| 2008/0077188 A1 | 3/2008 | Denker et al. |
| 2008/0091089 A1 | 4/2008 | Guillory et al. |
| 2008/0091114 A1 | 4/2008 | Min |
| 2008/0097549 A1 | 4/2008 | Colbaugh |
| 2008/0097917 A1 | 4/2008 | Dicks |
| 2008/0103440 A1 | 5/2008 | Ferren et al. |
| 2008/0114224 A1 | 5/2008 | Bandy et al. |
| 2008/0119705 A1 | 5/2008 | Patel |
| 2008/0119716 A1 | 5/2008 | Boric-Lubecke |
| 2008/0121825 A1 | 5/2008 | Trovato et al. |
| 2008/0137566 A1 | 6/2008 | Marholev |
| 2008/0139907 A1 | 6/2008 | Rao et al. |
| 2008/0140403 A1 | 6/2008 | Hughes et al. |
| 2008/0146871 A1 | 6/2008 | Arneson et al. |
| 2008/0146889 A1 | 6/2008 | Young |
| 2008/0146892 A1 | 6/2008 | LeBoeuf |
| 2008/0154104 A1 | 6/2008 | Lamego |
| 2008/0166992 A1 | 7/2008 | Ricordi |
| 2008/0175898 A1 | 7/2008 | Jones et al. |
| 2008/0183245 A1 | 7/2008 | Van Oort |
| 2008/0188837 A1 | 8/2008 | Belsky et al. |
| 2008/0194912 A1 | 8/2008 | Trovato et al. |
| 2008/0208009 A1 | 8/2008 | Shklarski |
| 2008/0214901 A1 | 9/2008 | Gehman |
| 2008/0214985 A1 | 9/2008 | Yanaki |
| 2008/0243020 A1 | 10/2008 | Chou |
| 2008/0249360 A1 | 10/2008 | Li |
| 2008/0262320 A1 | 10/2008 | Schaefer et al. |
| 2008/0262336 A1 | 10/2008 | Ryu |
| 2008/0269664 A1 | 10/2008 | Trovato et al. |
| 2008/0275312 A1 | 11/2008 | Mosesov |
| 2008/0284599 A1* | 11/2008 | Zdeblick et al. ............ 340/572.1 |
| 2008/0288027 A1 | 11/2008 | Kroll |
| 2008/0294020 A1 | 11/2008 | Sapounas |
| 2008/0299197 A1 | 12/2008 | Toneguzzo et al. |
| 2008/0300572 A1 | 12/2008 | Rankers |
| 2008/0303638 A1 | 12/2008 | Nguyen |
| 2008/0306357 A1 | 12/2008 | Korman |
| 2008/0306359 A1 | 12/2008 | Zdeblick et al. |
| 2008/0306360 A1 | 12/2008 | Robertson et al. |
| 2008/0311852 A1 | 12/2008 | Hansen |
| 2008/0312522 A1 | 12/2008 | Rowlandson |
| 2008/0316020 A1 | 12/2008 | Robertson |
| 2009/0009330 A1 | 1/2009 | Sakama et al. |
| 2009/0009332 A1 | 1/2009 | Nunez et al. |
| 2009/0024045 A1 | 1/2009 | Prakash |
| 2009/0024112 A1 | 1/2009 | Edwards et al. |
| 2009/0030293 A1 | 1/2009 | Cooper et al. |
| 2009/0030297 A1 | 1/2009 | Miller |
| 2009/0034209 A1 | 2/2009 | Joo |
| 2009/0043171 A1 | 2/2009 | Rule |
| 2009/0048498 A1 | 2/2009 | Riskey |
| 2009/0062634 A1 | 3/2009 | Say et al. |
| 2009/0062670 A1 | 3/2009 | Sterling |
| 2009/0069642 A1 | 3/2009 | Gao |
| 2009/0069655 A1 | 3/2009 | Say et al. |
| 2009/0069656 A1 | 3/2009 | Say et al. |
| 2009/0069657 A1 | 3/2009 | Say et al. |
| 2009/0069658 A1 | 3/2009 | Say et al. |
| 2009/0076343 A1 | 3/2009 | James |
| 2009/0082645 A1 | 3/2009 | Hafezi et al. |
| 2009/0087483 A1 | 4/2009 | Sison |
| 2009/0088618 A1 | 4/2009 | Ameson |
| 2009/0099435 A1 | 4/2009 | Say et al. |
| 2009/0105561 A1 | 4/2009 | Boyden et al. |
| 2009/0110148 A1 | 4/2009 | Zhang |
| 2009/0112626 A1 | 4/2009 | Talbot |
| 2009/0124871 A1 | 5/2009 | Arshak |
| 2009/0131774 A1 | 5/2009 | Sweitzer |
| 2009/0135886 A1 | 5/2009 | Robertson et al. |
| 2009/0157113 A1 | 6/2009 | Marcotte |
| 2009/0157358 A1 | 6/2009 | Kim |
| 2009/0161602 A1 | 6/2009 | Matsumoto |
| 2009/0163789 A1 | 6/2009 | Say et al. |
| 2009/0171180 A1 | 7/2009 | Pering |
| 2009/0173628 A1 | 7/2009 | Say et al. |
| 2009/0177055 A1 | 7/2009 | Say et al. |
| 2009/0177056 A1 | 7/2009 | Say et al. |
| 2009/0177057 A1 | 7/2009 | Say et al. |
| 2009/0177058 A1 | 7/2009 | Say et al. |
| 2009/0177059 A1 | 7/2009 | Say et al. |
| 2009/0177060 A1 | 7/2009 | Say et al. |
| 2009/0177061 A1 | 7/2009 | Say et al. |
| 2009/0177062 A1 | 7/2009 | Say et al. |

(56) References Cited

U.S. PATENT DOCUMENTS

| | | |
|---|---|---|
| 2009/0177063 A1 | 7/2009 | Say et al. |
| 2009/0177064 A1 | 7/2009 | Say et al. |
| 2009/0177065 A1 | 7/2009 | Say et al. |
| 2009/0177066 A1 | 7/2009 | Say et al. |
| 2009/0182206 A1 | 7/2009 | Najafi |
| 2009/0182207 A1 | 7/2009 | Riskey et al. |
| 2009/0182212 A1 | 7/2009 | Say et al. |
| 2009/0182213 A1 | 7/2009 | Say et al. |
| 2009/0182214 A1 | 7/2009 | Say et al. |
| 2009/0182215 A1 | 7/2009 | Say et al. |
| 2009/0182388 A1 | 7/2009 | Von Arx |
| 2009/0187088 A1 | 7/2009 | Say et al. |
| 2009/0187089 A1 | 7/2009 | Say et al. |
| 2009/0187090 A1 | 7/2009 | Say et al. |
| 2009/0187091 A1 | 7/2009 | Say et al. |
| 2009/0187092 A1 | 7/2009 | Say et al. |
| 2009/0187093 A1 | 7/2009 | Say et al. |
| 2009/0187094 A1 | 7/2009 | Say et al. |
| 2009/0187095 A1 | 7/2009 | Say et al. |
| 2009/0187381 A1 | 7/2009 | King et al. |
| 2009/0192351 A1 | 7/2009 | Nishino |
| 2009/0192368 A1 | 7/2009 | Say et al. |
| 2009/0192369 A1 | 7/2009 | Say et al. |
| 2009/0192370 A1 | 7/2009 | Say et al. |
| 2009/0192371 A1 | 7/2009 | Say et al. |
| 2009/0192372 A1 | 7/2009 | Say et al. |
| 2009/0192373 A1 | 7/2009 | Say et al. |
| 2009/0192374 A1 | 7/2009 | Say et al. |
| 2009/0192375 A1 | 7/2009 | Say et al. |
| 2009/0192376 A1 | 7/2009 | Say et al. |
| 2009/0192377 A1 | 7/2009 | Say et al. |
| 2009/0192378 A1 | 7/2009 | Say et al. |
| 2009/0192379 A1 | 7/2009 | Say et al. |
| 2009/0198115 A1 | 8/2009 | Say et al. |
| 2009/0198116 A1 | 8/2009 | Say et al. |
| 2009/0198175 A1 | 8/2009 | Say et al. |
| 2009/0203964 A1 | 8/2009 | Shimizu et al. |
| 2009/0203971 A1 | 8/2009 | Sciarappa |
| 2009/0203972 A1 | 8/2009 | Heneghan |
| 2009/0203978 A1 | 8/2009 | Say et al. |
| 2009/0204265 A1 | 8/2009 | Hackett |
| 2009/0210164 A1 | 8/2009 | Say et al. |
| 2009/0216101 A1 | 8/2009 | Say et al. |
| 2009/0216102 A1 | 8/2009 | Say et al. |
| 2009/0227204 A1 | 9/2009 | Robertson et al. |
| 2009/0227876 A1 | 9/2009 | Tran |
| 2009/0227940 A1 | 9/2009 | Say et al. |
| 2009/0227941 A1 | 9/2009 | Say et al. |
| 2009/0227988 A1 | 9/2009 | Wood et al. |
| 2009/0228214 A1 | 9/2009 | Say et al. |
| 2009/0231125 A1 | 9/2009 | Baldus |
| 2009/0234200 A1 | 9/2009 | Husheer |
| 2009/0243833 A1 | 10/2009 | Huang |
| 2009/0253960 A1 | 10/2009 | Takenaka et al. |
| 2009/0256702 A1 | 10/2009 | Robertson |
| 2009/0264714 A1 | 10/2009 | Chou |
| 2009/0264964 A1 | 10/2009 | Abrahamson |
| 2009/0265186 A1 | 10/2009 | Tarassenko et al. |
| 2009/0273467 A1 | 11/2009 | Elixmann |
| 2009/0281539 A1 | 11/2009 | Selig |
| 2009/0295548 A1 | 12/2009 | Ronkka |
| 2009/0296677 A1 | 12/2009 | Mahany |
| 2009/0303920 A1 | 12/2009 | Mahany |
| 2009/0306633 A1 | 12/2009 | Trovato et al. |
| 2009/0312619 A1 | 12/2009 | Say et al. |
| 2009/0318303 A1 | 12/2009 | Delamarche et al. |
| 2009/0318761 A1 | 12/2009 | Rabinovitz |
| 2009/0318779 A1 | 12/2009 | Tran |
| 2009/0318783 A1 | 12/2009 | Rohde |
| 2009/0318793 A1 | 12/2009 | Datta |
| 2010/0001841 A1 | 1/2010 | Cardullo |
| 2010/0010330 A1 | 1/2010 | Rankers |
| 2010/0033324 A1 | 2/2010 | Shimizu et al. |
| 2010/0049004 A1 | 2/2010 | Edman et al. |
| 2010/0049006 A1 | 2/2010 | Magar |
| 2010/0049012 A1 | 2/2010 | Dijksman et al. |
| 2010/0049069 A1 | 2/2010 | Tarassenko et al. |
| 2010/0056878 A1 | 3/2010 | Partin |
| 2010/0056891 A1 | 3/2010 | Say et al. |
| 2010/0056939 A1 | 3/2010 | Tarassenko et al. |
| 2010/0057041 A1 | 3/2010 | Hayter |
| 2010/0062709 A1 | 3/2010 | Kato |
| 2010/0063438 A1 | 3/2010 | Bengtsson |
| 2010/0063841 A1 | 3/2010 | D'Ambrosia et al. |
| 2010/0069002 A1 | 3/2010 | Rong |
| 2010/0069717 A1 | 3/2010 | Hafezi et al. |
| 2010/0081894 A1* | 4/2010 | Zdeblick et al. .............. 600/302 |
| 2010/0099967 A1 | 4/2010 | Say et al. |
| 2010/0099968 A1 | 4/2010 | Say et al. |
| 2010/0099969 A1 | 4/2010 | Say et al. |
| 2010/0100077 A1 | 4/2010 | Rush |
| 2010/0100078 A1 | 4/2010 | Say et al. |
| 2010/0106001 A1 | 4/2010 | Say et al. |
| 2010/0118853 A1 | 5/2010 | Godfrey |
| 2010/0139672 A1 | 6/2010 | Kroll et al. |
| 2010/0168659 A1 | 7/2010 | Say et al. |
| 2010/0179398 A1 | 7/2010 | Say et al. |
| 2010/0185055 A1 | 7/2010 | Robertson |
| 2010/0191073 A1 | 7/2010 | Tarassenko et al. |
| 2010/0210299 A1 | 8/2010 | Gorbachov |
| 2010/0222652 A1 | 9/2010 | Cho |
| 2010/0228113 A1 | 9/2010 | Solosko |
| 2010/0233026 A1 | 9/2010 | Ismagilov et al. |
| 2010/0234706 A1 | 9/2010 | Gilland |
| 2010/0234715 A1 | 9/2010 | Shin |
| 2010/0234914 A1 | 9/2010 | Shen |
| 2010/0239616 A1 | 9/2010 | Hafezi et al. |
| 2010/0245091 A1 | 9/2010 | Singh |
| 2010/0249881 A1 | 9/2010 | Corndorf |
| 2010/0256461 A1 | 10/2010 | Mohamedali |
| 2010/0259543 A1 | 10/2010 | Tarassenko et al. |
| 2010/0268048 A1 | 10/2010 | Say et al. |
| 2010/0268049 A1 | 10/2010 | Say et al. |
| 2010/0268050 A1 | 10/2010 | Say et al. |
| 2010/0274111 A1 | 10/2010 | Say et al. |
| 2010/0280345 A1 | 11/2010 | Say et al. |
| 2010/0280346 A1 | 11/2010 | Say et al. |
| 2010/0295694 A1 | 11/2010 | Kauffman et al. |
| 2010/0298668 A1 | 11/2010 | Hafezi et al. |
| 2010/0298730 A1 | 11/2010 | Tarassenko et al. |
| 2010/0312188 A1 | 12/2010 | Robertson et al. |
| 2010/0312580 A1 | 12/2010 | Tarassenko et al. |
| 2011/0009715 A1 | 1/2011 | O'Reilly et al. |
| 2011/0054265 A1 | 3/2011 | Hafezi et al. |
| 2011/0065983 A1 | 3/2011 | Hafezi et al. |
| 2011/0077660 A1 | 3/2011 | Janik et al. |
| 2011/0105864 A1 | 5/2011 | Robertson et al. |
| 2011/0124983 A1 | 5/2011 | Kroll et al. |
| 2011/0224912 A1 | 9/2011 | Bhavaraju et al. |
| 2011/0230732 A1 | 9/2011 | Edman et al. |
| 2012/0062371 A1 | 3/2012 | Radivojevic et al. |
| 2012/0299723 A1 | 11/2012 | Hafezi et al. |

FOREIGN PATENT DOCUMENTS

| | | |
|---|---|---|
| EP | 1534054 | 5/2005 |
| EP | 1702553 | 9/2006 |
| EP | 1789128 | 5/2007 |
| EP | 2143369 | 1/2010 |
| JP | 61072712 | 4/1986 |
| JP | 05-228128 | 9/1993 |
| JP | 2000-506410 | 5/2000 |
| JP | 2002263185 | 9/2002 |
| JP | 2004-313242 | 11/2004 |
| JP | 2005-073886 | 3/2005 |
| JP | 2005-087552 | 4/2005 |
| JP | 2005-304880 | 4/2005 |
| JP | 2005124708 | 5/2005 |
| JP | 2006006377 | 1/2006 |
| JP | 2006509574 | 3/2006 |
| JP | 2007-313340 | 12/2007 |
| JP | 2008011865 | 1/2008 |
| WO | WO8802237 | 4/1988 |
| WO | WO9221307 | 12/1992 |

(56) References Cited

FOREIGN PATENT DOCUMENTS

| | | |
|---|---|---|
| WO | WO9308734 | 5/1993 |
| WO | WO9319667 | 10/1993 |
| WO | WO9401165 | 1/1994 |
| WO | WO9739963 | 10/1997 |
| WO | WO9843537 | 10/1998 |
| WO | WO9937290 | 7/1999 |
| WO | WO9937920 | 7/1999 |
| WO | WO9959465 | 11/1999 |
| WO | WO0033246 | 6/2000 |
| WO | WO0100085 | 1/2001 |
| WO | WO0147466 | 7/2001 |
| WO | WO0174011 | 10/2001 |
| WO | WO0180731 | 11/2001 |
| WO | WO0245489 | 6/2002 |
| WO | WO02058330 | 7/2002 |
| WO | WO02062276 | 8/2002 |
| WO | WO02087681 | 11/2002 |
| WO | WO02095351 | 11/2002 |
| WO | WO03005877 | 1/2003 |
| WO | WO03050643 | 6/2003 |
| WO | WO03068061 | 8/2003 |
| WO | WO2004014225 | 2/2004 |
| WO | WO2004019172 | 3/2004 |
| WO | WO2004039256 | 5/2004 |
| WO | WO2004059551 | 7/2004 |
| WO | WO2004066833 | 8/2004 |
| WO | WO2004066834 | 8/2004 |
| WO | WO2004066903 | 8/2004 |
| WO | WO2004068881 | 8/2004 |
| WO | WO2004109316 | 12/2004 |
| WO | WO2005011237 | 2/2005 |
| WO | WO2005020023 | 3/2005 |
| WO | WO2005024687 | 3/2005 |
| WO | WO2005047837 | 5/2005 |
| WO | WO2005051166 | 6/2005 |
| WO | WO2005083621 | 9/2005 |
| WO | WO2005110238 | 11/2005 |
| WO | WO2006021932 | 3/2006 |
| WO | WO2006027586 | 3/2006 |
| WO | WO2006028347 | 3/2006 |
| WO | WO2006046648 | 5/2006 |
| WO | WO2006055892 | 5/2006 |
| WO | WO2006055956 | 5/2006 |
| WO | WO2006075016 | 7/2006 |
| WO | WO2006100620 | 9/2006 |
| WO | WO2006116718 | 11/2006 |
| WO | WO2006127355 | 11/2006 |
| WO | WO2007001724 | 1/2007 |
| WO | WO2007001742 | 1/2007 |
| WO | WO2007013952 | 2/2007 |
| WO | WO2007014084 | 2/2007 |
| WO | WO2007014527 | 2/2007 |
| WO | WO2007021496 | 2/2007 |
| WO | WO2007027660 | 3/2007 |
| WO | WO2007028035 | 3/2007 |
| WO | WO2007036687 | 4/2007 |
| WO | WO2007036741 | 4/2007 |
| WO | WO2007036746 | 4/2007 |
| WO | WO2007040878 | 4/2007 |
| WO | WO2007067054 | 6/2007 |
| WO | WO2007071180 | 6/2007 |
| WO | WO2007096810 | 8/2007 |
| WO | WO2007101141 | 9/2007 |
| WO | WO2007115087 | 10/2007 |
| WO | WO2007120946 | 10/2007 |
| WO | WO2007127316 | 11/2007 |
| WO | WO2007127879 | 11/2007 |
| WO | WO2007128165 | 11/2007 |
| WO | WO2007130491 | 11/2007 |
| WO | WO2007143535 | 12/2007 |
| WO | WO2007149546 | 12/2007 |
| WO | WO2006104843 | 1/2008 |
| WO | WO2008008281 | 1/2008 |
| WO | WO2008030482 | 3/2008 |
| WO | WO2008052136 | 5/2008 |
| WO | WO2008063626 | 5/2008 |
| WO | WO2008066617 | 6/2008 |
| WO | WO2008076464 | 6/2008 |
| WO | WO2008089232 | 7/2008 |
| WO | WO2008091683 | 7/2008 |
| WO | WO2008095183 | 8/2008 |
| WO | WO2008097652 | 8/2008 |
| WO | WO2008101107 | 8/2008 |
| WO | WO2008112577 | 9/2008 |
| WO | WO2008112578 | 9/2008 |
| WO | WO2008120156 | 10/2008 |
| WO | WO2008133394 | 11/2008 |
| WO | WO2008134185 | 11/2008 |
| WO | WO2008150633 | 12/2008 |
| WO | WO2009001108 | 12/2008 |
| WO | WO2009006615 | 1/2009 |
| WO | WO2009029453 | 3/2009 |
| WO | WO2009036334 | 3/2009 |
| WO | WO2009051829 | 4/2009 |
| WO | WO2009051830 | 4/2009 |
| WO | WO2009063377 | 5/2009 |
| WO | WO2009081348 | 7/2009 |
| WO | WO2009111664 | 9/2009 |
| WO | WO2009146082 | 12/2009 |
| WO | WO2010000085 | 1/2010 |
| WO | WO2010009100 | 1/2010 |
| WO | WO2010011833 | 1/2010 |
| WO | WO2010019778 | 2/2010 |
| WO | WO2010057049 | 5/2010 |
| WO | WO2010080765 | 7/2010 |
| WO | WO2010080843 | 7/2010 |
| WO | WO2010107563 | 9/2010 |
| WO | WO2010132331 | 11/2010 |
| WO | WO2010135516 | 11/2010 |
| WO | WO2011068963 | 6/2011 |
| WO | WO2011133799 | 10/2011 |
| WO | WO2011159336 | 12/2011 |
| WO | WO2011159337 | 12/2011 |
| WO | WO2011159338 | 12/2011 |
| WO | WO2011159339 | 12/2011 |

OTHER PUBLICATIONS

Winter, J. et al. "The material properties of gelatin gels"; USA Ballistic Research Laboratories, Mar. (1975), p. 1-157.

Kim et al., "A Semi-Interpenetrating Network System for a Polymer Membrane"; Eur. Polym. J. vol. 33 No. 7; pp. 1009-1014 (1997).

AADE, "AADE 37th Annual Meeting San Antonio Aug. 4-7, 2010" American Association of Diabetes Educators (2010); http://www.diabeteseducator.org/annualmeeting/2010/index.html; 2 pp.

Arshak et al., A Review and Adaptation of Methods of Object Tracking to Telemetry Capsules IC-Med (2007) vol. 1, No. 1, Issue 1, pp. 35 of 46.

"ASGE Technology Status Evaluation Report: wireless capsule endoscopy" American Soc. for Gastrointestinal Endoscopy (2006) vol. 63, No. 4; 7 pp.

Aydin et al., "Design and implementation considerations for an advanced wireless interface in miniaturized integrated sensor Microsystems" Sch. of Eng. & Electron., Edinburgh Univ., UK; (2003); abstract.

Barrie, Heidelberg pH capsule gastric analysis. Texbook of Natural Medicine, (1992), Pizzorno, Murray & Barrie.

Bohidar et al., "Dielectric Behavior of Gelatin Solutions and Gels" Colloid Polym Sci (1998) 276:81-86.

Brock, "Smart Medicine: The Application of Auto-ID Technology to Healthcare" Auto-ID Labs (2002) http://www.autoidlabs.org/uploads/media/MIT-AUTOID-WH-010.pdf.

Carlson et al., "Evaluation of a non-invasive respiratory monitoring system for sleeping subjects" Physiological Measurement (1999) 20(1): 53.

Coury, L. "Conductance Measurement Part 1: Theory"; Current Separations, 18:3 (1999) p. 91-96.

Delvaux et al., "Capsule endoscopy: Technique and indications" Clinical Gastroenterology (2008) vol. 22, Issue 5, pp. 813-837.

Dhar et al., "Electroless nickel plated contacts on porous silicon" Appl. Phys. Lett. 68 (10) pp. 1392-1393 (1996).

(56) References Cited

OTHER PUBLICATIONS

Eldek A., "Design of double dipole antenna with enhanced usable bandwidth for wideband phased array applications" Progress in Electromagnetics Research PIER 59, 1-15 (2006).

Fawaz et al., "Enhanced Telemetry System using CP-QPSK Band-Pass Modulation Technique Suitable for Smart Pill Medical Application" IFIP IEEE Dubai Conference (2008); http://www.asic.fh-offenburg.de/downloads/ePille/IFIP_IEEE_Dubai_Conference.pdf.

Ferguson et al., "Dialectric Constant Studies III Aqueous Gelatin Solutions" J. Chem. Phys. 2, 94 (1934) p. 94-98.

Furse C. M., "Dipole Antennas" J. Webster (ed). Wiley Encyclopedia of Electrical and Electronics Engineering (1999) p. 575-581.

Gilson, D.R. "Molecular dynamics simulation of dipole interactions", Department of Physics, Hull University, Dec. (2002), p. 1-43.

Given Imaging, "Agile Patency Brochure" (2006) http://www.inclino.no/documents/AgilePatencyBrochure_Global_GMB-0118-01.pdf; 4pp.

Gonzalez-Guillaumin et al., "Ingestible capsule for impedance and pH monitoring in the esophagus" IEEE Trans Biomed Eng. (2007) 54(12): 2231-6; abstract.

Greene, "Edible RFID microchip monitor can tell if you take your medicine" Bloomberg Businessweek (2010) 2 pp.; http://www.businessweek.com/idg/2010-03-31/edible-rfid-microchip-monitor-can-tell-if-you-take-your-medicine.html.

Heydari et al., "Analysis of the PLL jitter due to power/ground and substrate noise"; IEEE Transactions on Circuits and Systems (2004) 51(12): 2404-16.

ISFET—Ion Sensitive Field-Effect Transistor; Microsens S.A. pdf document. 4pp.

Intromedic, MicroCam Innovative Capsule Endoscope Pamphlet. (2006) 8 pp (http://www.intromedic.com/en/product/productinfo.asp).

Juvenile Diabetes Research Foundation International (JDRF), "Artificial Pancreas Project" (2010); http://www.artificialpancreasproject.com/; 3 pp.

Kamada K., "Electrophoretic deposition assisted by soluble anode" Materials Letters 57 (2003) 2348-2351.

Li, P-Y, et al. "An electrochemical intraocular drug delivery device", Sensors and Actuators A 143 (2008) p. 41-48.

LifeScan, "OneTouch UltraLink™" http://www.lifescan.com/products/meters/ultralink (2010) 2 pp.

Mackay et al., "Radio Telemetering from within the Body" Inside Information is Revealed by Tiny Transmitters that can be Swallowed or Implanted in Man or Animal Science (1991) 1196-1202; 134; American Association for the Advancement of Science, Washington D.C.

Mackay et al., "Endoradiosonde" Nature, (1957) 1239-1240, 179 Nature Publishing Group.

McKenzie et al., "Validation of a new telemetric core temperature monitor" J. Therm. Biol. (2004) 29(7-8):605-11.

Medtronic, "CareLink Therapy Management Software for Diabetes" (2010); https://carelink.minimed.com/patient/entry.jsp?bhcp=1; 1 pp.

Medtronic, "Carelink™ USB" (2008) http://www.medtronicdiabetes.com/pdf/carelink_usb_factsheet.pdf 2pp.

Medtronic "The New MiniMed Paradigm® REAL-Time Revel™ System" (2010) http://www.medtronicdiabetes.com/products/index.html; 2 pp.

Medtronic, "Mini Med Paradigm® Revel™ Insulin Pump" (2010) http://www.medtronicdiabetes.com/products/insulinpumps/index.html; 2 pp.

Medtronic, Mini Med Paradigm™ Veo™ System: Factsheet (2010). http://www.medtronic-diabetes.com.au/downloads/Paradigm%20Veo%20Factsheet.pdf ; 4 pp.

Melanson, "Walkers swallow RFID pills for science" Engadget (2008); http://www.engadget.com/2008/07/29/walkers-swallow-rfid-pills-for-science/.

Minimitter Co. Inc. "Actiheart" Traditional 510(k) Summary. Sep. 27, 2005.

Minimitter Co. Inc. Noninvasive technology to help your studies succeed. MiniMitter.com Mar. 31, 2009.

Mini Mitter Co, Inc. 510(k) Premarket Notification Mini-Logger for Diagnostic Spirometer. Sep. 21, 1999.

Mini Mitter Co, Inc. 510(k) Premarket Notification for VitalSense. Apr. 22, 2004.

Minimitter Co. Inc. VitalSense Integrated Physiological Monitoring System. Product Description. (2005).

Minimitter Co. Inc. VitalSense Wireless Vital Signs Monitoring. Temperatures.com Mar. 31, 2009.

Mohaverian et al., "Estimation of gastric residence time of the Heidelberg capsule in humans: effect of varying food composition" Gastroenterology (1985) 89:(2): 392-7.

"New 'smart pill' to track adherence" E-Health-Insider (2010) http://www.e-health-insider.com/news/5910/new_'smart pill'_monitors_medicines.

NPL_AntennaBasics.pdf, Radio Antennae, http://www.erikdeman.de/html/sail018h.htm; (2008) 3pp.

O'Brien et al., "The Production and Characterization of Chemically Reactive Porous Coatings of Zirconium Via Unbalanced Magnetron Sputtering" Surface and Coatings Technology (1996) 86-87; 200-206.

Park, "Medtronic to Buy MiniMed for $3.7 Billion" (2001) HomeCare; http://homecaremag.com/mag/medical_medtronic_buy_minimed/; 2 pp.

Philips Respironics (http/minimitter.com/products.cfm) Products, Noninvasive Technology to Help Your Studies Succeed. 510(k) Permanent Notification for Vital Sense. Apr. 22, 2004.

"RFID "pill" monitors marchers" RFID News (2008) http://www.rfidnews.org/2008/07/23/rfid-pill-monitors-marchers/.

Roulstone, et al., "Studies on Polymer Latex Films: I. A study of latex film morphology" Polymer International 24 (1991) pp. 87-94.

Sanduleanu et al., "Octave tunable, highly linear, RC-ring oscillator with differential fine-coarse tuning, quadrature outputs and amplitude control for fiber optic transceivers" (2002) IEEE MTT-S International Microwave Symposium Digest 545-8.

Santini, J.T. et al, "Microchips as controlled drug delivery-devices", Agnew. Chem. Int. Ed. (2000), vol. 39, p. 2396-2407.

"SensiVida minimally invasive clinical systems" Investor Presentation Oct. (2009) 28pp; http://www.sensividamedtech.com/SensiVidaGeneralOctober09.pdf.

Shawgo, R.S. et al. "BioMEMS from drug delivery", Current Opinion in Solid State and Material Science 6 (2002), p. 329-334.

Shin et al., "A Simple Route to Metal Nanodots and Nanoporous Metal Films"; Nano Letters, vol. 2, No. 9 (2002) pp. 933-936.

Shrivas et al., "A New Platform for Bioelectronics-Electronic Pill", Cummins College, (2010).; http://www.cumminscollege.org/downloads/electronics_and_telecommunication/Newsletters/Current%20Newsletters.pdf; First cited in third party client search conducted by Patent Eagle Search May 18, 2010.

"Smartlife awarded patent for knitted transducer" Innovation in Textiles News: http://www.innovationintextiles.com/articles/208.php; 2pp. (2009).

"The SmartPill Wireless Motility Capsule" SmartPill, The Measure of GI Health; (2010) http://www.smartpillcorp.com/index.cfm?pagepath=Products/The_SmartPill_Capsule&id=17814.

Solanas et al., "RFID Technology for the Health Care Sector" Recent Patents on Electrical Engineering (2008) 1, 22-31.

Soper, S.A. et al. "Bio-Mems Technologies and Applications", Chapter 12, "MEMS for Drug Delivery", p. 325-346 (2007).

Swedberg, "University Team Sees Ingestible RFID Tag as a Boon to Clinical Trials" RFID Journal Apr. 27, 2010; http://www.rfidjournal.com/article/view/7560/1.

Tajalli et al., "Improving the power-delay performance in subthreshold source-coupled logic circuits" Integrated Circuit and System Design. Power and Timing Modeling, Optimization and Simulation, Springer Berlin Heidelberg (2008) 21-30.

Tatbul et al., "Confidence-based data management for personal area sensor networks" ACM International Conference Proceeding Series (2004) 72.

Tierney, M.J. et al "Electroreleasing Composite Membranes for Delivery of Insulin and other Biomacromolecules", J. Electrochem. Soc., vol. 137, No. 6, Jun. 1990, p. 2005-2006.

(56) References Cited

OTHER PUBLICATIONS

University of Florida News "Rx for health: Engineers design pill that signals it has been swallowed" (2010) 2pp.; http://news.ufl.edu/2010/03/31/antenna-pill-2/.

U.S. Appl. No. 12/238,345, filed Sep. 25, 2008, Hooman et al., Non-Final Office Action mailed Jun. 13, 2011 22pp.

Walkey, "MOSFET Struture and Processing"; 97.398* Physical Electronics Lecture 20; 24 pp.

Watson, et al., "Determination of the relationship between the pH and conductivity of gastric juice" Physiol Meas. 17 (1996) pp. 21-27.

Wongmanerod et al., "Determination of pore size distribution and surface area of thin porous silicon layers by spectroscopic ellipsometry" Applied Surface Science 172 (2001) 117-125.

Xiaoming et al., "A telemedicine system for wireless home healthcare based on bluetooth and the internet" Telemedicine Journal and e-health (2004) 10(S2): S110-6.

Yang et al., "Fast-switching frequency synthesizer with a discriminator-aided phase detector" IEEE Journal of Solid-State Circuits (2000) 35(10): 1445-52.

Yao et al., "Low Power Digital Communication in Implantable Devices Using Volume Conduction of Biological Tissues" Proceedings of the 28th IEEE, EMBS Annual International Conference, Aug. 30-Sep. 3, 2006.

Zimmerman, "Personal Area Networks: Near-field intrabody communication" IBM Systems Journal (1996) 35 (3-4):609-17.

Description of ePatch Technology Platform for ECG and EMG, located it http://www.madebydelta.com/imported/images/DELTA_Web/documents/ME/ePatch_ECG_EMG.pdf, Dated Sep. 2, 2010.

Zworkin, "A Radio Pill" Nature, (1957) 898, 179 Nature Publishing Group.

Gaglani S. "Put Your Phone, or Skin, on Vibrate" MedGadget (2012) http://medgadget.com/2012/03/put-your-phone-or-skin-on-vibrate.html 8pp.

Jimbo et al., "Gastric-fluid-utilized micro battery for micro medical devices" The Sixth International Workshop on Micro and Nanotechnology for Power Geneartion and Energy Conservation Applications, (2006) pp. 97-100.

Rolison et al., "Electrically conductive oxide aerogels: new materials in electrochemistry" J. Mater. Chem. (2001) 1, 963-980.

Shrivas et al., "A New Platform for Bioelectronics-Electronic Pill", Cummins College, (2010). http://www.cumminscollege.org/downloads/electronics_and_telecommunication/Newsletters/Current%20Newsletters.pdf; (2010).

Walkey, "MOSFET Structure and Processing"; 97.398* Physical Electronics Lecture 20; 24 pp.

Halthion Medical Technologies "Providing Ambulatory Medical Devices Which Monitor, Measure and Record" webpage. Online website: http://www.halthion.com/; downloaded May 30, 2012.

Hoeksma, J. "New 'smart pill' to track adherence" E-Health-Insider May 2010 http://www.e-health-insider.com/news/5910/new_'smart_pill'_monitors_medicines.

Jung, S. "Dissolvable 'Transient Electronics' Will Be Good for Your Body and the Environment" MedGadget; Oct. 1, 2012; Onlne website: http://medgadget.com/2012/10/dissolvable-transient-electronics-will-be-good-for-your-body-and-the-environment.html; downloaded Oct. 24, 2012; 4 pp.

Platt, D., "Modulation and Deviation" AE6EO, Foothills Amateur Radio Society; Oct. 26, 2007; 61 pp.

* cited by examiner

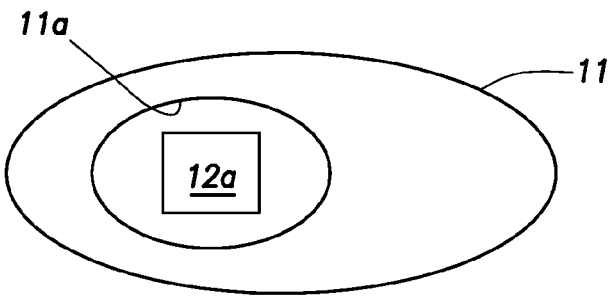
FIG.2C
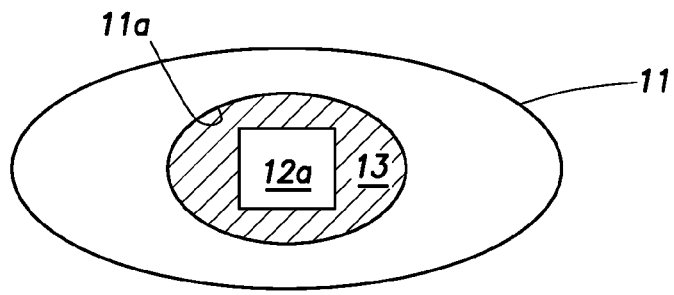
FIG.2D
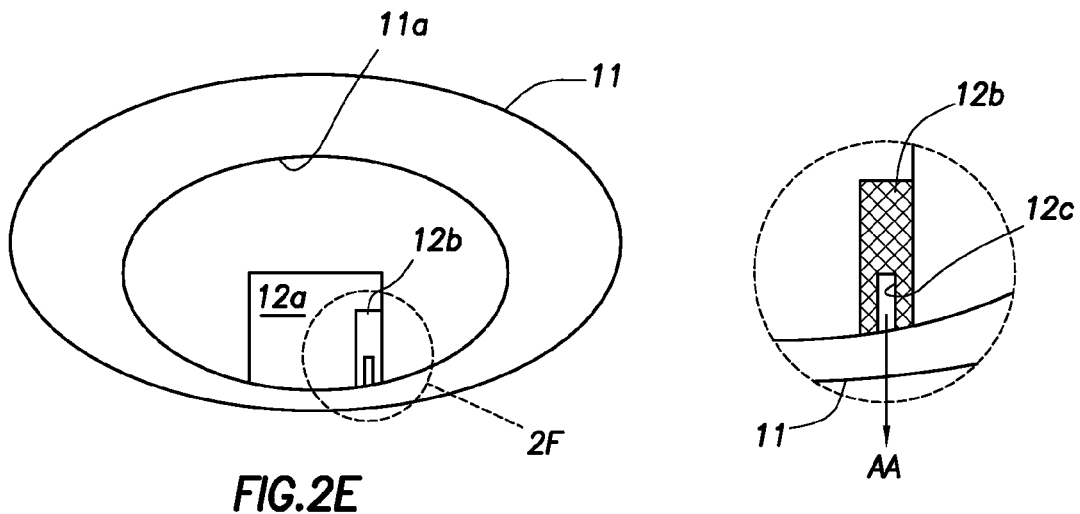
FIG.2E
FIG.2F

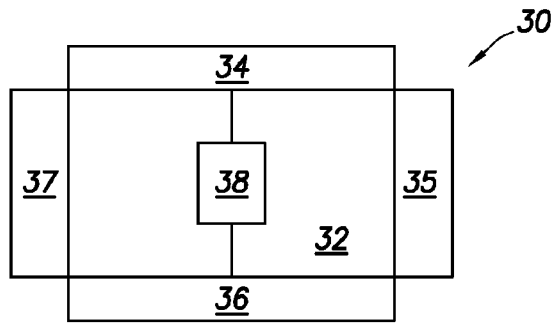
FIG.3
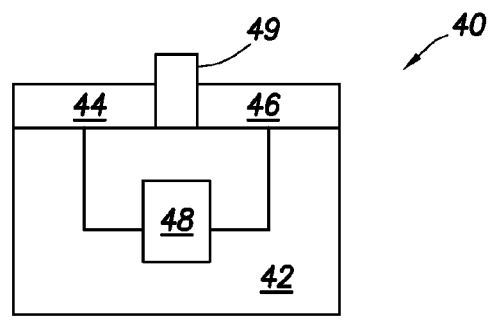
FIG.4
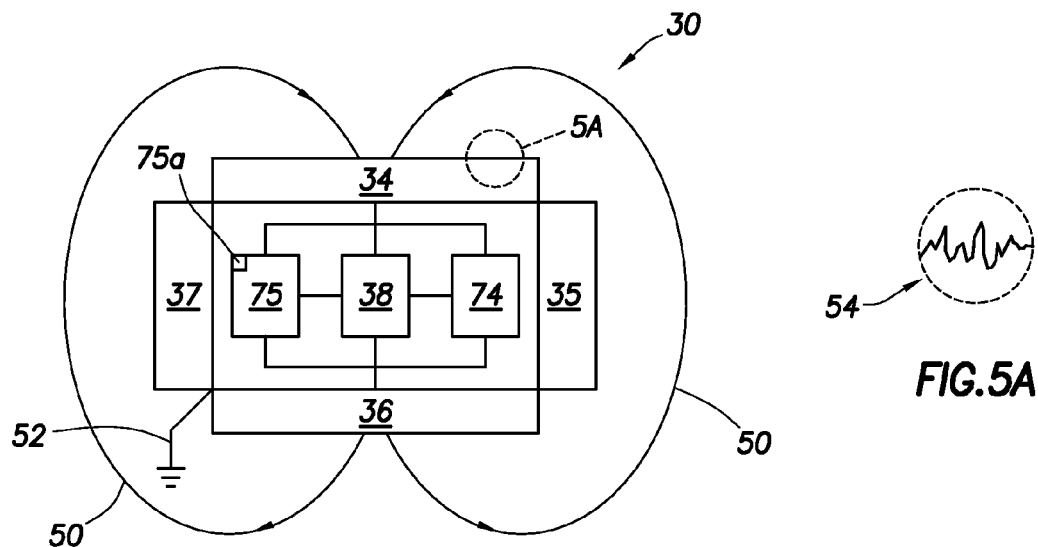
FIG.5
FIG.5A

COMMUNICATION SYSTEM WITH REMOTE ACTIVATION

CROSS-REFERENCE TO RELATED APPLICATIONS

This application is related to U.S. patent application Ser. No. 12/564,017, filed on Sep. 21, 2009 and entitled "Communication System with Partial Power Source", published on Apr. 1, 2010 as U.S. Publication No. US2010-0081894A1, which is a continuation-in-part application of U.S. patent application Ser. No. 11/912,475 filed Jun. 23, 2008 and entitled "Pharma-Informatics System", published on Nov. 20, 2008 as U.S. Publication No. 2008-0284599A1 which application is a 371 application of PCT Application No. PCT/US06/16370 filed Apr. 28, 2006 and entitled "Pharma-Informatics System"; which application pursuant to 35 U.S.C. §119 (e), claims priority to the filing dates of: U.S. Provisional Patent Application Ser. No. 60/676,145 filed Apr. 28, 2005 and entitled "Pharma-Informatics System"; U.S. Provisional Patent Application Ser. No. 60/694,078, filed Jun. 24, 2005, and entitled "Pharma-Informatics System"; U.S. Provisional Patent Application Ser. No. 60/713,680 filed Sep. 1, 2005 and entitled "Medical Diagnostic And Treatment Platform Using Near-Field Wireless Communication Of Information Within A Patient's Body"; and U.S. Provisional Patent Application Ser. No. 60/790,335 filed Apr. 7, 2006 and entitled "Pharma-Informatics System"; the disclosures of which are herein incorporated by reference.

This application is related to the following US Applications filed concurrently herewith, the disclosures of which are incorporated herein by reference: U.S. application Ser. No. 13/180,498 COMMUNICATION SYSTEM WITH MULTIPLE TYPES OF POWER; U.S. application Ser. No. 13/180,539 COMMUNICATION SYSTEM USING AN IMPLANTABLE DEVICE; U.S. application Ser. No. 13/180,525 COMMUNICATION SYSTEM WITH ENHANCED PARTIAL POWER AND METHOD OF MANUFACTURING SAME; U.S. application Ser. No. 13/180,538 COMMUNICATION SYSTEM USING POLYPHARMACY CO-PACKAGED MEDICATION DOSING UNIT; and U.S. application Ser. No. 13/180/507 Communication System Incorporated in an INGESTIBLE PRODUCT.

FIELD

The present invention is related to communication systems for detection of an event. More specifically, the present disclosure includes a system that includes a device with various power sources and communication schemes.

INTRODUCTION

Ingestible devices that include electronic circuitry have been proposed for use in a variety of different medical applications, including both diagnostic and therapeutic applications. These devices typically require an internal power supply for operation. Examples of such ingestible devices are ingestible electronic capsules which collect data as they pass through the body, and transmit the data to an external receiver system. An example of this type of electronic capsule is an in-vivo video camera. The swallowable capsule includes a camera system and an optical system for imaging an area of interest onto the camera system. The transmitter transmits the video output of the camera system and the reception system receives the transmitted video output. Other examples include an ingestible imaging device, which has an internal and self-contained power source, which obtains images from within body lumens or cavities. The electronic circuit components of the device are enclosed by an inert indigestible housing (e.g. glass housing) that passes through the body internally. Other examples include an ingestible data recorder capsule medical device. The electronic circuits of the disclosed device (e.g. sensor, recorder, battery etc.) are housed in a capsule made of inert materials.

In other examples, fragile radio frequency identification (RFID) tags are used in drug ingestion monitoring applications. In order for the RFID tags to be operational, each application/tag requires an internal power supply. The RFID tags are antenna structures that are configured to transmit a radio-frequency signal through the body.

The problem these existing devices pose is that the power source is internal to device and such power sources are bulky, costly to produce and potentially harmful to the surrounding environment if the power source leaks or is damaged. Additionally, having antennas extending from the device is a concern as related to the antennas getting damaged or causing a problem when the device is used in-vivo. Therefore, what is needed is suitable system with circuitry that eliminates the need for an internal power source and antennas.

SUMMARY

The present disclosure includes a system for producing a unique signature that indicates the occurrence of an event. The system includes circuitry and components that can be placed within certain environments that include a conducting fluid. One example of such an environment is inside a container that houses the conducting fluid, such as a sealed bag with a solution, which includes an IV bag. Another example is within the body of a living organism, such as an animal or a human. The systems are ingestible and/or digestible or partially digestible. The system includes dissimilar materials positioned on the framework such that when a conducting fluid comes into contact with the dissimilar materials, a voltage potential difference is created. The voltage potential difference, and hence the voltage, is used to power up control logic that is positioned within the framework. Ions or current flows from the first dissimilar material to the second dissimilar material via the control logic and then through the conducting fluid to complete a circuit. The control logic controls the conductance between the two dissimilar materials and, hence, controls or modulates the conductance of the system.

As the ingestible circuitry is made up of ingestible, and even digestible, components, the ingestible circuitry results in little, if any, unwanted side effects, even when employed in chronic situations. Examples of the range of components that may be included are: logic and/or memory elements; effectors; a signal transmission element; and a passive element, such as a resistor or inductor. The one or more components on the surface of the support may be laid out in any convenient configuration. Where two or more components are present on the surface of the solid support, interconnects may be provided. All of the components and the support of the ingestible circuitry are ingestible, and in certain instances digestible or partially digestible.

BRIEF DESCRIPTION OF THE FIGURES

FIG. 2C shows a capsule with the event indicator system positioned inside in accordance with one aspect of the present invention.

FIG. 2D shows a capsule with the event indicator system positioned inside in accordance with one aspect of the present invention.

FIG. 2E shows a capsule with the event indicator system positioned inside in accordance with one aspect of the present invention.

FIG. 2F is an exploded view of the event indicator system.

FIG. 3 is a block diagram representation of one aspect of the event indicator system with dissimilar metals positioned on opposite ends.

FIG. 4 is a block diagram representation of another aspect of the event indicator system with dissimilar metals positioned on the same end and separated by a non-conducting material.

FIG. 5 shows ionic transfer or the current path through a conducting fluid when the event indicator system of FIG. 3 is in contact with conducting liquid and in an active state.

FIG. 5A shows an exploded view of the surface of dissimilar materials of FIG. 5.

DETAILED DESCRIPTION

The present disclosure includes multiple aspects for indicating the occurrence of an event. As described in more detail below, a system of the present invention is used with a conducting fluid to indicate the event marked by contact between the conducting fluid and the system. For example, the system of the present disclosure may be used with pharmaceutical product and the event that is indicated is when the product is taken or ingested. The term "ingested" or "ingest" or "ingesting" is understood to mean any introduction of the system internal to the body. For example, ingesting includes simply placing the system in the mouth all the way to the descending colon. Thus, the term ingesting refers to any instant in time when the system is introduced to an environment that contains a conducting fluid. Another example would be a situation when a non-conducting fluid is mixed with a conducting fluid. In such a situation the system would be present in the non-conduction fluid and when the two fluids are mixed, the system comes into contact with the conducting fluid and the system is activated. Yet another example would be the situation when the presence of certain conducting fluids needed to be detected. In such instances, the presence of the system, which would be activated, within the conducting fluid could be detected and, hence, the presence of the respective fluid would be detected.

Referring again to the instance where the system is used with the product that is ingested into the living organism, when the product that includes the system is taken or ingested, the device comes into contact with the conducting liquid of the body. When the system of the present invention comes into contact with the body fluid, a voltage potential is created and the system is activated. A portion of the power source is provided by the device, while another portion of the power source is provided by the conducting fluid, which is discussed in detail below.

Figure 1:
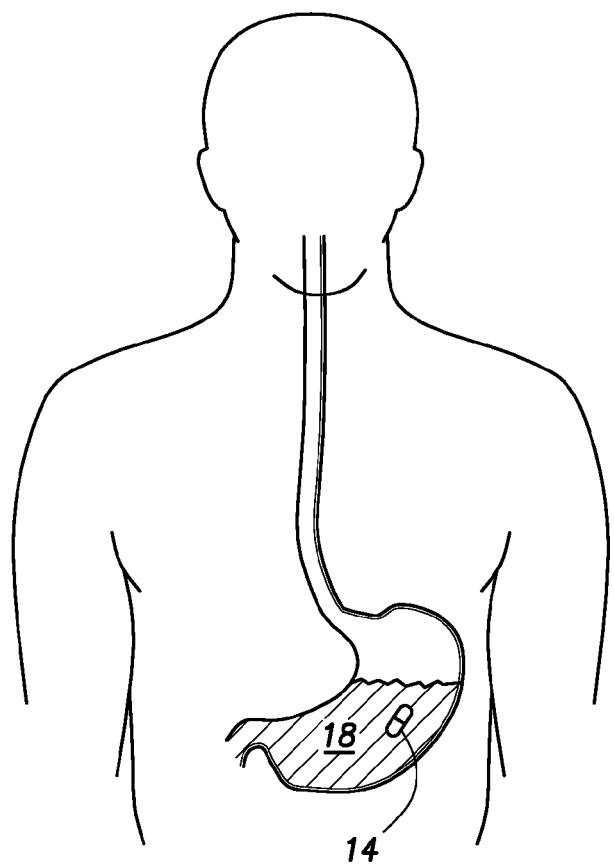
FIG. 1 shows a pharmaceutical product with an event indicator system according to the teaching of the present invention, wherein the product and the event indicator system combination are within the body.

Referring now to FIG. 1, an ingestible product 14 that includes a system of the present invention is shown inside the body. The product 14 is configured as an orally ingestible pharmaceutical formulation in the form of a pill or capsule. Upon ingestion, the pill moves to the stomach. Upon reaching the stomach, the product 14 is in contact with stomach fluid 18 and undergoes a chemical or electrochemical reaction with the various materials in the stomach fluid 18, such as hydrochloric acid and other digestive agents. The system of the present invention is discussed in reference to a pharmaceutical environment. However, the scope of the present invention is not limited thereby. The present invention can be used in any environment e.g., outside a body, where a conducting fluid is present or becomes present through mixing of two or more components that result in a conducting liquid.

Figure 2A:
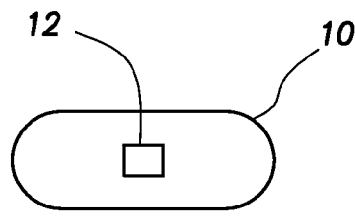
FIG. 2A shows the pharmaceutical product of FIG. 1 with the event indicator system on the exterior of the pharmaceutical product.

Referring now to FIG. 2A, a pharmaceutical product 10, similar to the product 14 of FIG. 1, is shown with a system 12, such as an ingestible event marker or an ionic emission module (IEM). The scope of the present invention is not limited by the shape or type of the product 10. For example, it will be clear to one skilled in the art that the product 10 can be a capsule, a time-release oral dosage, a tablet, a gel cap, a sub-lingual tablet, or any oral dosage product that can be combined with the system 12. In the referenced aspect, the product 10 has the system 12 secured to the exterior using known methods of securing micro-devices to the exterior of pharmaceutical products. Example of methods for securing the micro-device to the product is disclosed in U.S. Provisional application Ser. No. 12/741,583 filed on Jan. 5, 2010 and entitled "HIGH-THROUGHPUT PRODUCTION OF INGESTIBLE EVENT MARKERS" also filed as PCT Application No. PCT/US10/20142 dated Jan. 5, 2010 and published as WO 2010/080765 dated Jul. 15, 2010 as well as U.S. Provisional Application No. 61/177,611 filed on May 12, 2009 and entitled "INGESTIBLE EVENT MARKERS COMPRISING AN IDENTIFIER AND AN INGESTIBLE COMPONENT", also filed as PCT Application No. PCT/US10/34186 dated May 10, 2010 and published as WO 2010/132331 dated Nov. 18, 2010 the entire disclosure of each is incorporated herein by reference. Once ingested, the system 12 comes into contact with body liquids and the system 12 is activated. The system 12 uses the voltage potential difference to power up and thereafter modulates conductance to create a unique and identifiable current signature. Upon activation, the system 12 controls the conductance and, hence, current flow to produce the current signature.

There are various reasons for delaying the activation of the system 12. In order to delay the activation of the system 12, the system 12 may be coated with a shielding material or protective layer. The layer is dissolved over a period of time, thereby allowing the system 12 to be activated when the product 10 has reached a target location.

Figure 2B:
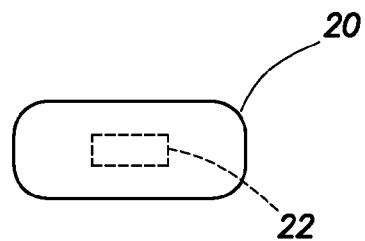
FIG. 2B shows the pharmaceutical product of FIG. 1 with the event indicator system positioned inside the pharmaceutical product.

Referring now to FIG. 2B, a pharmaceutical product 20, similar to the product 14 of FIG. 1, is shown with a system 22, such as an ingestible event marker or an identifiable emission module. The scope of the present invention is not limited by the environment to which the system 22 is introduced. For example, the system 22 can be enclosed in a capsule that is taken in addition to/independently from the pharmaceutical product. The capsule may be simply a carrier for the system 22 and may not contain any product. Furthermore, the scope of the present invention is not limited by the shape or type of product 20. For example, it will be clear to one skilled in the art that the product 20 can be a capsule, a time-release oral dosage, a tablet, a gel capsule, a sub-lingual tablet, or any oral dosage product. In the referenced aspect, the product 20 has the system 22 positioned inside or secured to the interior of the product 20. In one aspect, the system 22 is secured to the interior wall of the product 20. When the system 22 is positioned inside a gel capsule, then the content of the gel capsule is a non-conducting gel-liquid. On the other hand, if the content of the gel capsule is a conducting gel-liquid, then in an alternative aspect, the system 22 is coated with a protective cover to prevent unwanted activation by the gel capsule content. If the content of the capsule is a dry powder or microspheres, then the system 22 is positioned or placed within the capsule. If the product 20 is a tablet or hard pill, then the system 22 is held in place inside the tablet. Once ingested, the product 20 containing the system 22 is disintegrated and/or dissolved. The system 22 comes into contact with body liquids and the system 22 is activated. Depending on the product 20, the system 22 may be positioned in either a near-central or near-perimeter position depending on the desired activation delay between the time of initial ingestion and activation of the system 22. For example, a central position for the system 22 means that it will take longer for the system 22 to be in contact with the conducting liquid and, hence, it will take longer for the system 22 to be activated. Therefore, it will take longer for the occurrence of the event to be detected.

Referring now to FIG. 2C, in accordance with one aspect of the present invention, a capsule 11 is shown with a cavity 11a therein. The capsule 11 is shown as an empty capsule in accordance with one aspect of the present invention. Inside the cavity is a system 12a, which is similar to the systems 12 and 22 of FIGS. 2A and 2B, respectively. As the capsule 11 is introduced to or comes into contact with a conducting fluid, the capsule 11 breaks apart or disintegrates or dissolves to allow the system to be released from the environment.

Referring now to FIG. 2D, the capsule 11 is shown with the system 12a along with a material 13 inserted into the cavity 11a. The material 13 can be activated to expand and cause the capsule 11 to break apart. In accordance with one aspect of the present invention, the activation of the material 13 is controlled by the system 12a. The system 12a, as shown in FIG. 2E below, receives a signal from an external source which may be inside the body, on the body or outside the body and in response to the signal, is able to activate the material 13 to cause the material 12 to expand. For example, in accordance with one aspect of the present invention, the material 13 is an electroactive material that is selected to be reactive to an electrical signal such that the properties change when exposed to a voltage potential or current. An electroactive material or matrix includes a material whose properties, such as physical dimensions or solubility, change in response to an applied voltage or current. Examples of electroactive materials include: polyvinylidene fluoride (PVDF), perfluorinated sulfouic acid (Nafion™), perfluorinated carboxylic acid (Flemion™), cellulose, a polymer matrix (for example polyethylene oxide or cellulose) containing a salt (eg a salt containing a multivalent ion such as $Fe^{3+}$) or a protein. In accordance with another aspect of the present invention, the system 12a includes a plunger that releases a chemical or compound into the material 11a to cause a chemical reaction that causes the material 11a to expand.

Referring now to FIG. 2E, the capsule 11 is shown with the system 12a in greater detail. The system 12a includes a unit 12b secured to the system 12a. In accordance with one aspect of the present invention, the unit 12b includes a housing that defines a cavity 12c. In one example, the cavity 12c can be filled with a chemical or a compound that is released into the cavity 11a when the cavity 11a is filled with the material 13 to initiate a reaction that causes the material 13 to expand. Referring now also to FIG. 2F, in another example, the cavity 12c includes a solid object that acts like a needle or a rod. The object is mechanically pushed out of the cavity 12c in the direction AA as shown. The object is then able to push through the wall of the capsule 11 and cause the wall to tear or break apart. This facilitates separation of the system 12a from the capsule 11 and allows the system 12a to come into contact with the surrounding environment and become activated. Thus, the unit 12b is able to control activation of the system 12a.

In accordance with one aspect of the present invention, the unit 12b includes a communication module that can either receive, transmit, or receive and transmit. Thus, the unit 12b can act as a secondary communication module, as discussed in detail below with respect to FIG. 5 and element 75. The unit 12b can receive control signals from and external source, in accordance with one aspect of the present invention. In accordance with another aspect, the unit 12b can send signals to an external source. In accordance with yet another aspect of the present invention, the unit 12b acts as a transceiver and is able to receive and send signals to external devices. The unit 12b is also in communication with the other components of the system 12a as discussed in detail below.

Referring now to FIG. 3, in one aspect, the systems 12 and 22 of FIGS. 2A and 2B, respectively, are shown in more detail as system 30. The system 30 can be used in association with any pharmaceutical product, as mentioned above, to determine when a patient ingests the pharmaceutical product. As indicated above, the scope of the present invention is not limited by the environment and the product that is used with the system 30. For example, the system 30 may be placed within a capsule and the capsule is placed within the conducting liquid. The capsule would then dissolve over a period of time and release the system 30 into the conducting liquid. Thus, in one aspect, the capsule would contain the system 30 and no product. Such a capsule may then be used in any environment where a conducting liquid is present and with any product. For example, the capsule may be dropped into a container filled with jet fuel, salt water, tomato sauce, motor oil, or any similar product. Additionally, the capsule containing the system 30 may be ingested at the same time that any pharmaceutical product is ingested in order to record the occurrence of the event, such as when the product was taken.

In the specific example of the system 30 combined with the pharmaceutical product, as the product or pill is ingested, the system 30 is activated. The system 30 controls conductance to produce a unique current signature that is detected, thereby signifying that the pharmaceutical product has been taken. The system 30 includes a resistance 31 between the $V_{high}$ and ground 52. The resistive element includes a known quantity and represents a voltage drop between $V_{high}$ and ground. This known quantity is used to determine the impedance of the surrounding environment as noted with respect to FIG. 5 below and unit 75a.

The system 30 includes a framework 32. The framework 32 is a chassis for the system 30 and multiple components are attached to, deposited upon, or secured to the framework 32. In this aspect of the system 30, an ingestible or digestible material 34 is physically associated with the framework 32. The material 34 may be chemically deposited on, evaporated onto, secured to, or built-up on the framework all of which may be referred to herein as "deposit" with respect to the framework 32. The material 34 is deposited on one side of the framework 32. The materials of interest that can be used as material 34 include, but are not limited to: Cu or CuI. The material 34 is deposited by physical vapor deposition, electrodeposition, or plasma deposition, among other protocols. The material 34 may be from about 0.05 to about 500 μm thick, such as from about 5 to about 100 μm thick. The shape is controlled by shadow mask deposition, or photolithography and etching. Additionally, even though only one region is shown for depositing the material, each system 30 may contain two or more electrically unique regions where the material 34 may be deposited, as desired.

At a different side, which is the opposite side as shown in FIG. 3, another digestible material 36 is deposited, such that materials 34 and 36 are dissimilar and are insulated from each other. Although not shown, the different side selected may be the side next to the side selected for the material 34. The scope of the present invention is not limited by the side selected and the term "different side" can mean any of the multiple sides that are different from the first selected side. Furthermore, even though the shape of the system is shown as a square, the shape maybe any geometrically suitable shape. Material 34 and 36 are selected such that they produce a voltage potential difference when the system 30 is in contact with conducting liquid, such as body fluids. The materials of interest for material 36 include, but are not limited to: Mg, Zn, or other electronegative metals. As indicated above with respect to the material 34, the material 36 may be chemically deposited on, evaporated onto, secured to, or built-up on the framework. Also, an adhesion layer may be necessary to help the material 36 (as well as material 34 when needed) to adhere to the framework 32. Typical adhesion layers for the material 36 are Ti, TiW, Cr or similar material. Anode material and the adhesion layer may be deposited by physical vapor deposition, electrodeposition or plasma deposition. The material 36 may be from about 0.05 to about 500 μm thick, such as from about 5 to about 100 μm thick. However, the scope of the present invention is not limited by the thickness of any of the materials nor by the type of process used to deposit or secure the materials to the framework 32.

According to the disclosure set forth, the materials 34 and 36 can be any pair of materials with different electrochemical potentials. Additionally, in the aspects wherein the system 30 is used in-vivo, the materials 34 and 36 may be vitamins that can be absorbed. More specifically, the materials 34 and 36 can be made of any two materials appropriate for the environment in which the system 30 will be operating. For example, when used with an ingestible product, the materials 34 and 36 are any pair of materials with different electrochemical potentials that are ingestible. An illustrative example includes the instance when the system 30 is in contact with an ionic solution, such as stomach acids. Suitable materials are not restricted to metals, and in certain aspects the paired materials are chosen from metals and non-metals, e.g., a pair made up of a metal (such as Mg) and a salt (such as CuCl or CuI). With respect to the active electrode materials, any pairing of substances—metals, salts, or intercalation compounds—with suitably different electrochemical potentials (voltage) and low interfacial resistance are suitable.

Materials and pairings of interest include, but are not limited to, those reported in Table 1 below. In one aspect, one or both of the metals may be doped with a non-metal, e.g., to enhance the voltage potential created between the materials as they come into contact with a conducting liquid. Non-metals that may be used as doping agents in certain aspects include, but are not limited to: sulfur, iodine and the like. In another aspect, the materials are copper iodine (CuI) as the anode and magnesium (Mg) as the cathode. Aspects of the present invention use electrode materials that are not harmful to the human body.

TABLE 1

|  | Anode | Cathode |
|---|---|---|
| Metals | Magnesium, Zinc Sodium, Lithium Iron | |
| Salts | | Copper salts: iodide, chloride, bromide, sulfate, formate, (other anions possible) $Fe^{3+}$ salts: e.g. orthophosphate, pyrophosphate, (other anions possible) Oxygen or Hydrogen ion (H+) on platinum, gold or other catalytic surfaces |
| Intercalation compounds | Graphite with Li, K, Ca, Na, Mg | Vanadium oxide Manganese oxide |

Thus, when the system 30 is in contact with the conducting liquid, a current path, an example is shown in FIG. 5, is formed through the conducting liquid between material 34 and 36. A control device 38 is secured to the framework 32 and electrically coupled to the materials 34 and 36. The control device 38 includes electronic circuitry, for example control logic that is capable of controlling and altering the conductance between the materials 34 and 36.

The voltage potential created between the materials 34 and 36 provides the power for operating the system as well as produces the current flow through the conducting fluid and the system. In one aspect, the system operates in direct current mode. In an alternative aspect, the system controls the direction of the current so that the direction of current is reversed in a cyclic manner, similar to alternating current. As the system reaches the conducting fluid or the electrolyte, where the fluid or electrolyte component is provided by a physiological fluid, e.g., stomach acid, the path for current flow between the materials 34 and 36 is completed external to the system 30; the current path through the system 30 is controlled by the control device 38. Completion of the current path allows for the current to flow and in turn a receiver, not shown, can detect the presence of the current and recognize that the system 30 has been activate and the desired event is occurring or has occurred.

In one aspect, the two materials 34 and 36 are similar in function to the two electrodes needed for a direct current power source, such as a battery. The conducting liquid acts as the electrolyte needed to complete the power source. The completed power source described is defined by the electrochemical reaction between the materials 34 and 36 of the system 30 and enabled by the fluids of the body. The completed power source may be viewed as a power source that exploits electrochemical conduction in an ionic or a conducting solution such as gastric fluid, blood, or other bodily fluids and some tissues. Additionally, the environment may be something other than a body and the liquid may be any conducting liquid. For example, the conducting fluid may be salt water or a metallic based paint.

In certain aspects, these two materials are shielded from the surrounding environment by an additional layer of material. Accordingly, when the shield is dissolved and the two dissimilar materials are exposed to the target site, a voltage potential is generated.

In certain aspects, the complete power source or supply is one that is made up of active electrode materials, electrolytes, and inactive materials, such as current collectors, packaging, etc. The active materials are any pair of materials with different electrochemical potentials. Suitable materials are not restricted to metals, and in certain aspects the paired materials are chosen from metals and non-metals, e.g., a pair made up of a metal (such as Mg) and a salt (such as CuI). With respect to the active electrode materials, any pairing of substances—metals, salts, or intercalation compounds—with suitably different electrochemical potentials (voltage) and low interfacial resistance are suitable.

A variety of different materials may be employed as the materials that form the electrodes. In certain aspects, electrode materials are chosen to provide for a voltage upon contact with the target physiological site, e.g., the stomach, sufficient to drive the system of the identifier. In certain aspects, the voltage provided by the electrode materials upon contact of the metals of the power source with the target physiological site is 0.001 V or higher, including 0.01 V or higher, such as 0.1 V or higher, e.g., 0.3 V or higher, including 0.5 volts or higher, and including 1.0 volts or higher, where in certain aspects, the voltage ranges from about 0.001 to about 10 volts, such as from about 0.01 to about 10 V.

Referring again to FIG. 3, the materials 34 and 36 provide the voltage potential to activate the control device 38. Once the control device 38 is activated or powered up, the control device 38 can alter conductance between the materials 34 and 36 in a unique manner. By altering the conductance between materials 34 and 36, the control device 38 is capable of controlling the magnitude of the current through the conducting liquid that surrounds the system 30. This produces a unique current signature that can be detected and measured by a receiver (not shown), which can be positioned internal or external to the body. In addition to controlling the magnitude of the current path between the materials, non-conducting materials, membrane, or "skirt" are used to increase the "length" of the current path and, hence, act to boost the conductance path, as disclosed in the U.S. patent application Ser. No. 12/238,345 entitled, "In-Body Device with Virtual Dipole Signal Amplification" filed Sep. 25, 2008, and published as 2009-0082645 A1 dated Mar. 26, 2009 the entire content of which is incorporated herein by reference. Alternatively, throughout the disclosure herein, the terms "non-conducting material", "membrane", and "skirt" are used interchangeably with the term "current path extender" without impacting the scope or the present aspects and the claims herein. The skirt, shown in portion at 35 and 37, respectively, may be associated with, e.g., secured to, the framework 32. Various shapes and configurations for the skirt are contemplated as within the scope of the present invention. For example, the system 30 may be surrounded entirely or partially by the skirt and the skirt maybe positioned along a central axis of the system 30 or off-center relative to a central axis. Thus, the scope of the present invention as claimed herein is not limited by the shape or size of the skirt. Furthermore, in other aspects, the materials 34 and 36 may be separated by one skirt that is positioned in any defined region between the materials 34 and 36.

Referring now to FIG. 4, in another aspect, the systems 12 and 22 of FIGS. 2A and 2B, respectively, are shown in more detail as system 40. The system 40 includes a framework 42. The framework 42 is similar to the framework 32 of FIG. 3. In this aspect of the system 40, a digestible or dissolvable material 44 is deposited on a portion of one side of the framework 42. At a different portion of the same side of the framework 42, another digestible material 46 is deposited, such that materials 44 and 46 are dissimilar. More specifically, materials 44 and 46 are selected such that they form a voltage potential difference when in contact with a conducting liquid, such as body fluids. Thus, when the system 40 is in contact with and/or partially in contact with the conducting liquid, then a current path, an example is shown in FIG. 5, is formed through the conducting liquid between material 44 and 46. A control device 48 is secured to the framework 42 and electrically coupled to the materials 44 and 46. The control device 48 includes electronic circuitry that is capable of controlling part of the conductance path between the materials 44 and 46. The materials 44 and 46 are separated by a non-conducting skirt 49. Various examples of the skirt 49 are disclosed in U.S. Provisional Application No. 61/173,511 filed on Apr. 28, 2009 and entitled "HIGHLY RELIABLE INGESTIBLE EVENT MARKERS AND METHODS OF USING SAME" also filed as PCT Application No. PCT/US10/32590 dated Apr. 27, 2010 and published as WO 2010/129288 dated Nov. 11, 2010 and U.S. Provisional Application No. 61/173,564 filed on Apr. 28, 2009 and entitled "INGESTIBLE EVENT MARKERS HAVING SIGNAL AMPLIFIERS THAT COMPRISE AN ACTIVE AGENT" also filed as PCT Application No. PCT/US10/32590 dated Apr. 27, 2010 and published as WO 2010/129288 dated Nov. 11, 2010; as well as U.S. application Ser. No. 12/238,345 filed Sep. 25, 2008 and entitled "IN-BODY DEVICE WITH VIRTUAL DIPOLE SIGNAL AMPLIFICATION" and published as 2009-0082645 A1 dated Mar. 26, 2009; the entire disclosure of each is incorporated herein by reference.

Once the control device 48 is activated or powered up, the control device 48 can alter conductance between the materials 44 and 46. Thus, the control device 48 is capable of controlling the magnitude of the current through the conducting liquid that surrounds the system 40. As indicated above with respect to system 30, a unique current signature that is associated with the system 40 can be detected by a receiver (not shown) to mark the activation of the system 40. In order to increase the "length" of the current path the size and/or characteristics of the skirt 49 is altered. The longer the current path, the easier it may be for the receiver to detect the current.

Referring now to FIG. 5, the system 30 of FIG. 3 is shown in an activated state and in contact with conducting liquid. The system 30 is grounded through ground contact 52. For example, when the system 30 is in contact with a conducting fluid, the conducting fluid provides the ground. The system 30 also includes a sensor module 74, which is described in greater detail with respect to FIG. 6. Ion or current paths 50 are formed between material 34 to material 36 and through the conducting fluid in contact with the system 30. The voltage potential created between the material 34 and 36 is created through chemical reactions between materials 34/36 and the conducting fluid.

The system 30 also includes a unit 75. The unit 75 includes aspects that enable communication functions and in accordance with the various aspects of the present invention can act as any of the following: a receiver, a transmitter, or a transceiver. Thus, another device that is external to the system 30, such as a cell phone, an implanted device, a device attached to the user's body, or a device placed under the user's skin, may communicate, e.g. to, from or both, the system 30 through the unit 75. The unit 75 is also electrically connected to the materials 34 and 36. In accordance with one aspect of the present invention, any device that is external to the system 30 may communicate with either the unit 75 or the control module 38 using current flow through the environment surrounding the system 30. For example, a patch or receiver that is attached to the user's body, a cell phone or device being held by the user, or an implanted device, are examples of devices which can generate a current signature through the user's body. The current signature can include information that is encoded therein. The current signature is detected by the system 30, using the unit 75 or the control module 38, and decoded to allow communication to the system 30 from the device external to system 30. Accordingly, the external device can send a signal to the unit 75, either wirelessly or through transconduction, that controls the activation of the system 30.

In accordance with one aspect of the present invention, the unit 75 can also measure the surrounding environment, either directly or through the sensor module 74, to determine is the system 30 should be deactivate due to unfavorable environmental conditions. For example, the unit 75 may include an impedance measurement unit 75a that is able to measure impedance of the environment around the system 30. The unit 75a measures impedance by transmitting or applying voltage to one output terminal, such as the material 34. The unit 75a then measures impedance (using the resistance 31 of FIG. 3). With a known quantity of resistance and the known voltage, the unit 75a is able to determine the impedance of the surrounding environment. The received signal at the receiver is directly proportional to the current output of the system 30. If a variable resistance is added at the output terminal of the system 30, such as resistance 31, then the current output of the system 30 will be proportional to $1/(R+Z)$, where R is the value of the variable resistor and Z, the local impedance of the solution or stomach environment around the system 30. Therefore, the detected signal will be equal to:

$$V\text{received} = k/(R+Z)$$

The system 30 can be designed with a variable resistor that cycles between 2 or more levels during transmission. This results in a received signal that will vary according the above equation. When detected, the signal is used to generate a linear plot to fit:

$$1/V\text{received vs } R$$

and determine the slope and intercept. The slope will have a value $1/k$ and the intercept, $Z/k$. This allows both k and the local impedance of the system 30 to be determined, independent of the actual voltage or current draw from the system 30 because the value of the variable resistor is know from the design parameters.

The impedance measurement may be used to monitor hydration state of the patient, presence of drug, Gastro-intestinal motility/waves, gastric transit time, presence of certain types of tissue (tumors) or bleeding. The impedance measurement is also a useful diagnostic tool for monitoring performance of the system 30. For example, if the impedance of the surrounding environment would prevent effective communication, then the system 30 can be deactivated or activated with a delay. In accordance with one aspect of the present invention, the unit 75 sends a signal to the control device 38. In response, the control device 38 can alter the conductance, and hence the impedance, between the materials 34 and 36 to reduce the rate of chemical reaction between materials 34 and 36 and the surrounding environment and thereby cause the system 30 to reach a deactivated mode, state, or condition. In this way, even though there is some chemical reaction, it is sufficiently low to preserve the power of the system 30 for later use, while still allowing operation of sensing and measurement of the nearby environment.

If the conditions of the environment change to become favorable to communication, as determine by the measurements of the environment, then the unit 75 sends a signal to the control device 38 to alter the conductance between the materials 34 and 36 to allow for communication using the current signature of the system 30. Thus, if the system 30 has been deactivated and the impedance if the environment is suitable for communication, then the system 30 can be activated again.

If the conditions of the environment change to become favorable to communication, as determined by the measurements of the environment, then the unit 75 sends a signal to the control device 38 to alter the conductance between the materials 34 and 36 to allow for communication using the current signature of the system 30. Thus, if the system 30 has been deactivated and the impedance of the environment is suitable for communication, then the system 30 can be activated again.

Referring now to FIG. 5A, this shows an exploded view of the surface of the material 34. In one aspect, the surface of the material 34 is not planar, but rather an irregular surface. The irregular surface increases the surface area of the material and, hence, the area that comes in contact with the conducting fluid. In one aspect, at the surface of the material 34, there is an electrochemical reaction between the material 34 and the surrounding conducting fluid such that mass is exchanged with the conducting fluid. The term "mass" as used here includes any ionic or non-ionic species that may be added or removed from the conductive fluid as part of the electrochemical reactions occurring on material 34. One example includes the instant where the material is CuCl and when in contact with the conducting fluid, CuCl is converted to Cu metal (solid) and Cl— is released into the solution. The flow of positive ions into the conducting fluid is depicted by the current path 50. Negative ions flow in the opposite direction. In a similar manner, there is an electrochemical reaction involving the material 36 that results in ions released or removed from the conducting fluid. In this example, the release of negative ions at the material 34 and release of positive ions by the material 36 are related to each other through the current flow that is controlled by the control device 38. The rate of reaction and hence the ionic emission rate or current, is controlled by the control device 38. The control device 38 can increase or decrease the rate of ion flow by altering its internal conductance, which alters the impedance, and therefore the current flow and reaction rates at the materials 34 and 36. Through controlling the reaction rates, the system 30 can encode information in the ionic flow. Thus, the system 30 encodes information using ionic emission or flow.

The control device 38 can vary the duration of ionic flow or current while keeping the current or ionic flow magnitude near constant, similar to when the frequency is modulated and the amplitude is constant. Also, the control device 38 can vary the level of the ionic flow rate or the magnitude of the current flow while keeping the duration near constant. Thus, using various combinations of changes in duration and altering the rate or magnitude, the control device 38 encodes information in the current or the ionic flow. For example, the control device 38 may use, but is not limited to any of the following techniques, including Binary Phase-Shift Keying (PSK), Frequency modulation, Amplitude modulation, on-off keying, and PSK with on-off keying.

As indicated above, the various aspects disclosed herein, such as systems 30 and 40 of FIGS. 3 and 4, respectively, include electronic components as part of the control device 38 or the control device 48. Components that may be present include but are not limited to: logic and/or memory elements, an integrated circuit, an inductor, a resistor, and sensors for measuring various parameters. Each component may be secured to the framework and/or to another component. The components on the surface of the support may be laid out in any convenient configuration. Where two or more components are present on the surface of the solid support, interconnects may be provided.

As indicated above, the system, such as control devices 30 and 40, control the conductance between the dissimilar materials and, hence, the rate of ionic flow or current. Through altering the conductance in a specific manner the system is capable of encoding information in the ionic flow and the current signature. The ionic flow or the current signature is used to uniquely identify the specific system. Additionally, the systems 30 and 40 are capable of producing various different unique patterns or signatures and, thus, provide additional information. For example, a second current signature based on a second conductance alteration pattern may be used to provide additional information, which information may be related to the physical environment. To further illustrate, a first current signature may be a very low current state that maintains an oscillator on the chip and a second current signature may be a current state at least a factor of ten higher than the current state associated with the first current signature.

Figure 5B:
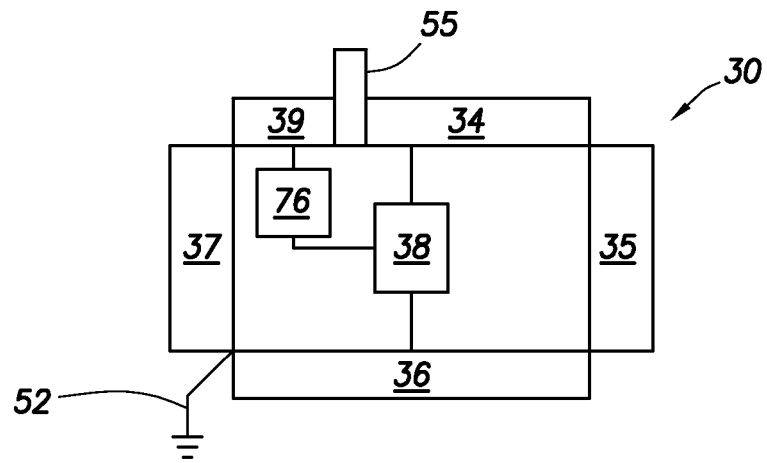
FIG. 5B shows the event indicator system of FIG. 5 with a pH sensor unit.
Figure 6:
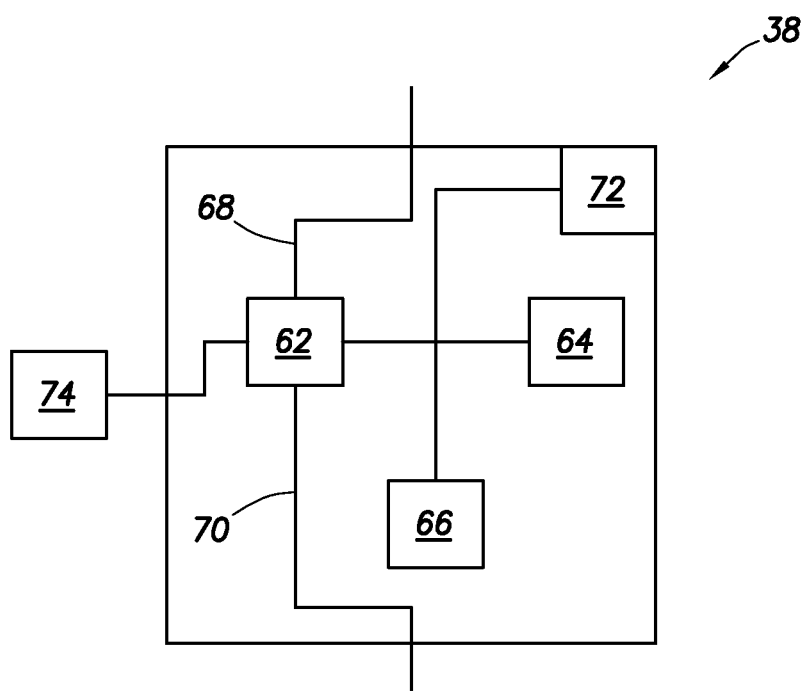
FIG. 6 is a block diagram illustration of one aspect of the control device used in the system of FIGS. 3 and 4.

Referring now to FIG. 6, a block diagram representation of the control device 38 is shown. The control device 38 includes a control module 62, a counter or clock 64, and a memory 66. Additionally, the device 38 is shown to include a sensor module 72 as well as the sensor module 74, which was referenced in FIG. 5. The control module 62 has an input 68 electrically coupled to the material 34 and an output 70 electrically coupled to the material 36. The control module 62, the clock 64, the memory 66, and the sensor modules 72/74 also have power inputs (some not shown). The power for each of these components is supplied by the voltage potential produced by the chemical reaction between materials 34 and 36 and the conducting fluid, when the system 30 is in contact with the conducting fluid. The control module 62 controls the conductance through logic that alters the overall impedance of the system 30. The control module 62 is electrically coupled to the clock 64. The clock 64 provides a clock cycle to the control module 62. Based upon the programmed characteristics of the control module 62, when a set number of clock cycles have passed, the control module 62 alters the conductance characteristics between materials 34 and 36. This cycle is repeated and thereby the control device 38 produces a unique current signature characteristic. The control module 62 is also electrically coupled to the memory 66. Both the clock 64 and the memory 66 are powered by the voltage potential created between the materials 34 and 36.

The control module 62 is also electrically coupled to and in communication with the sensor modules 72 and 74. In the aspect shown, the sensor module 72 is part of the control device 38 and the sensor module 74 is a separate component. In alternative aspects, either one of the sensor modules 72 and 74 can be used without the other and the scope of the present invention is not limited by the structural or functional location of the sensor modules 72 or 74. Additionally, any component of the system 30 may be functionally or structurally moved, combined, or repositioned without limiting the scope of the present invention as claimed. Thus, it is possible to have one single structure, for example a processor, which is designed to perform the functions of all of the following modules: the control module 62, the clock 64, the memory 66, and the sensor module 72 or 74. On the other hand, it is also within the scope of the present invention to have each of these functional components located in independent structures that are linked electrically and able to communicate.

Referring again to FIG. 6, the sensor modules 72 or 74 can include any of the following sensors: temperature, pressure, pH level, and conductivity. In one aspect, the sensor modules 72 or 74 gather information from the environment and communicate the analog information to the control module 62. The control module then converts the analog information to digital information and the digital information is encoded in the current flow or the rate of the transfer of mass that produces the ionic flow. In another aspect, the sensor modules 72 or 74 gather information from the environment and convert the analog information to digital information and then communicate the digital information to control module 62. In the aspect shown in FIG. 5, the sensor module 74 is shown as being electrically coupled to the material 34 and 36 as well as the control device 38. In another aspect, as shown in FIG. 6, the sensor module 74 is electrically coupled to the control device 38 at connection 78. The connection 78 acts as both a source for power supply to the sensor module 74 and a communication channel between the sensor module 74 and the control device 38.

Referring now to FIG. 5B, the system 30 includes a pH sensor module 76 connected to a material 39, which is selected in accordance with the specific type of sensing function being performed. The pH sensor module 76 is also connected to the control device 38. The material 39 is electrically isolated from the material 34 by a non-conductive barrier 55. In one aspect, the material 39 is platinum. In operation, the pH sensor module 76 uses the voltage potential difference between the materials 34/36. The pH sensor module 76 measures the voltage potential difference between the material 34 and the material 39 and records that value for later comparison. The pH sensor module 76 also measures the voltage potential difference between the material 39 and the material 36 and records that value for later comparison. The pH sensor module 76 calculates the pH level of the surrounding environment using the voltage potential values. The pH sensor module 76 provides that information to the control device 38. The control device 38 varies the rate of the transfer of mass that produces the ionic transfer and the current flow to encode the information relevant to the pH level in the ionic transfer, which can be detected by a receiver (not shown). Thus, the system 30 can determine and provide the information related to the pH level to a source external to the environment.

As indicated above, the control device 38 can be programmed in advance to output a pre-defined current signature. In another aspect, the system can include a receiver system that can receive programming information when the system is activated. In another aspect, not shown, the switch 64 and the memory 66 can be combined into one device.

In addition to the above components, the system 30 may also include one or other electronic components. Electrical components of interest include, but are not limited to: additional logic and/or memory elements, e.g., in the form of an integrated circuit; a power regulation device, e.g., battery, fuel cell or capacitor; a sensor, a stimulator, etc.; a signal transmission element, e.g., in the form of an antenna, electrode, coil, etc.; a passive element, e.g., an inductor, resistor, etc.

In certain aspects, the ingestible circuitry includes a coating layer. The purpose of this coating layer can vary, e.g., to protect the circuitry, the chip and/or the battery, or any components during processing, during storage, or even during ingestion. In such instances, a coating on top of the circuitry may be included. Also of interest are coatings that are designed to protect the ingestible circuitry during storage, but dissolve immediately during use. For example, coatings that dissolve upon contact with an aqueous fluid, e.g. stomach fluid, or the conducting fluid as referenced above. Also of interest are protective processing coatings that are employed to allow the use of processing steps that would otherwise damage certain components of the device. For example, in aspects where a chip with dissimilar material deposited on the top and bottom is produced, the product needs to be diced. However, the dicing process can scratch off the dissimilar material, and also there might be liquid involved which would cause the dissimilar materials to discharge or dissolve. In such instances, a protective coating on the materials prevents mechanical or liquid contact with the component during processing can be employed. Another purpose of the dissolvable coatings may be provided to delay activation of the device. For example, the coating that sits on the dissimilar material and takes a certain period of time, e.g., five minutes, to dissolve upon contact with stomach fluid may be employed. The coating can also be an environmentally sensitive coating, e.g., a temperature or pH sensitive coating, or other chemically sensitive coating that provides for dissolution in a controlled fashion and allows one to activate the device when desired. Coatings that survive the stomach but dissolve in the intestine are also of interest, e.g., where one desires to delay activation until the device leaves the stomach. An example of such a coating is a polymer that is insoluble at low pH, but becomes soluble at a higher pH. Also of interest are pharmaceutical formulation protective coatings, e.g., a gel cap liquid protective coating that prevents the circuit from being activated by liquid of the gel cap.

Identifiers of interest include two dissimilar electrochemical materials, which act similar to the electrodes (e.g., anode and cathode) of a power source. The reference to an electrode or anode or cathode are used here merely as illustrative examples. The scope of the present invention is not limited by the label used and includes the aspect wherein the voltage potential is created between two dissimilar materials. Thus, when reference is made to an electrode, anode, or cathode it is intended as a reference to a voltage potential created between two dissimilar materials.

When the materials are exposed and come into contact with the body fluid, such as stomach acid or other types of fluid (either alone or in combination with a dried conductive medium precursor), a potential difference, that is, a voltage, is generated between the electrodes as a result of the respective oxidation and reduction reactions incurred to the two electrode materials. A voltaic cell, or battery, can thereby be produced. Accordingly, in aspects of the invention, such power supplies are configured such that when the two dissimilar materials are exposed to the target site, e.g., the stomach, the digestive tract, etc., a voltage is generated.

In certain aspects, one or both of the metals may be doped with a non-metal, e.g., to enhance the voltage output of the battery. Non-metals that may be used as doping agents in certain aspects include, but are not limited to: sulfur, iodine and the like.

It is to be understood that this invention is not limited to particular embodiments or aspects described herein and, as such, may vary. It is also to be understood that the terminology used herein is for the purpose of describing particular aspects only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual aspects described and illustrated herein has discrete components and features which may be readily separated from or combined with the features of any of the other several aspects without departing from the scope or spirit of the present invention. Any recited method can be carried out in the order of events recited or in any other order which is logically possible.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and aspects of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary aspects shown and described herein. Rather, the scope and spirit of present invention is embodied by the appended claims.

What is claimed is:

1. A device for communication, the device comprising:
   a first communication unit comprising
      a support structure;
      a partial power source comprising a first material deposited onto the support structure; and a second material deposited onto the support structure and electrically isolated from the first material, wherein the first material and the second material are selected to have a voltage potential difference when in contact with a conductive fluid to provide power to activate the device;

a control module associated with the support structure and electrically connected to the first material and the second material and configured to control conductance between the first material and the second material, wherein, when the first material and the second material are in contact with the conductive fluid, a change in the conductance between the first material and the second material alters a current flow extending through the conductive fluid between the first material and the second material to thereby encode information in a current signature;

a second communication unit in communication with the control module and associated with the support structure to at least either receive a signal from an external source or send a signal to the external source;

a sealed housing defining a cavity, wherein the first and second communication units are positioned within the cavity; and a release material within the cavity, wherein the second communication unit generates a release command to cause the release material to expand and open the sealed housing to release the first communication unit into the conductive fluid to activate the partial power source and thereby activate the device.

2. The device of claim 1, wherein the second communication unit includes a mechanism that extends outward from the second communication unit to penetrate a wall portion of the sealed housing to allow the first communication unit to be separated from the sealed housing.

3. A device for communication, the device comprising:
a first communication unit comprising
a support structure;
a partial power source comprising
a first material deposited onto the support structure; and
a second material deposited onto the support structure and electrically isolated from the first material, wherein the first material and the second material are selected to have a voltage potential difference when in contact with a conductive fluid to provide power to activate the device;
a control module associated with the support structure and electrically connected to the first material and the second material and configured to control conductance between the first material and the second material, wherein, when the first material and the second material are in contact with the conductive fluid, a change in the conductance between the first material and the second material alters a current flow extending through the conductive fluid between the first material and the second material to thereby encode information in a current signature;
a second communication unit in communication with the control module and associated with the support structure to at least either receive a signal from an external source or send a signal to the external source, wherein the second communication unit includes a rod that is mechanically activated to tear a wall portion of a sealed housing and cause the sealed housing to open and allow the first communication unit to come into contact with the conducting fluid; and
the sealed housing defining a cavity, wherein the second communication unit is positioned within the cavity to release the first communication unit into the conductive fluid to activate the partial power source and to activate the device.

4. A device for communication, the device comprising:
a first communication unit comprising
a support structure;
a partial power source comprising
a first material deposited onto the support structure; and
a second material deposited onto the support structure and electrically isolated from the first material, wherein the first material and the second material are selected to have a voltage potential difference when in contact with a conductive fluid to provide power to activate the device;
a control module associated with the support structure and electrically connected to the first material and the second material and configured to control conductance between the first material and the second material, wherein, when the first material and the second material are in contact with the conductive fluid, a change in the conductance between the first material and the second material alters a current flow extending through the conductive fluid between the first material and the second material to thereby encode information in a current signature;
a second communication unit in communication with the control module and associated with the support structure to at least either receive a signal from an external source or send a signal to the external source, wherein the second communication unit measures at least one characteristic associated with an environment immediately surrounding the first communication unit; and
a release apparatus secured to the support structure and in communication with the second communication unit, wherein the second communication unit is configured to provide a release command to the release apparatus, and wherein the release apparatus is configured to cause the device to be exposed to the conducting fluid in response to the release command to release the first communication unit into the conductive fluid to activate the partial power source and thereby activate the device.

5. The device of claim 4, further comprising a sealed housing defining a cavity, wherein the first and second communication units are positioned within the cavity, and wherein the cavity includes a material that is in communication with the release apparatus and upon receiving the release command the release apparatus causes the material to expand within the cavity such that the sealed housing breaks apart causing the device to be exposed to the conducting fluid.

6. The device of claim 4, further comprising a sealed housing defining a cavity, wherein the first and second communication units are positioned within the cavity, and wherein the release apparatus includes an expanding material that expands within the cavity, upon receiving the release command, to cause the sealed housing to break apart causing the device to be exposed to the conducting fluid.

7. The device of claim 4, further comprising a sealed housing defining a cavity, wherein the first and second communication units are positioned within the cavity, and wherein the release apparatus includes a rod that is mechanically extended from the release apparatus within the cavity of the sealed housing when the release command is received to cause the sealed housing to break apart and cause the device to be exposed to the conducting fluid.

8. A device for communication, the device comprising:
a first communication unit comprising
   a support structure;
      a partial power source comprising
         a first material deposited onto the support structure; and
         a second material deposited onto the support structure and electrically isolated from the first material, wherein the first material and the second material are selected to have a voltage potential difference when in contact with a conductive fluid to provide power to activate the device;
   a control module associated with the support structure and electrically connected to the first material and the second material and configured to control conductance between the first material and the second material, wherein, when the first material and the second material are in contact with the conductive fluid, a change in the conductance between the first material and the second material alters a current flow extending through the conductive fluid between the first material and the second material to thereby encode information in a current signature;
a second communication unit in communication with the control module and associated with the support structure to at least either receive a signal from an external source or send a signal to the external source; and
a sealed housing defining a cavity, wherein the first and second communication units are positioned within the cavity and further comprising an electroactive matrix within the cavity, wherein the second communication unit generates voltage to cause the electroactive matrix to expand and open the sealed housing to release the first communication unit into the conductive fluid to activate the partial power source and thereby activate the device.

9. A device for communication, the device comprising:
a first communication unit comprising
   a support structure;
   a partial power source comprising
      a first material deposited onto the support structure; and
      a second material deposited onto the support structure and electrically isolated from the first material, wherein the first material and the second material are selected to have a voltage potential difference when in contact with a conductive fluid to provide power to activate the device;
   a control module associated with the support structure and electrically connected to the first material and the second material and configured to control conductance between the first material and the second material, wherein, when the first material and the second material are in contact with the conductive fluid, a change in the conductance between the first material and the second material alters a current flow extending through the conductive fluid between the first material and the second material to thereby encode information in a current signature; and
a second communication unit comprising an impedance measurement device configured to measure an impedance of an environment surrounding the device, the second communication unit in communication with the control module and associated with the support structure to at least either receive a signal from an external source or send a signal to the external source, wherein after the device comes into contact with the conducting fluid, the second communication unit sends a control signal to the control module, in response to the measured impedance, to adjust the conductance so as to deactivate the device or to activate the device with a delay.

* * * * *